`US008293211B2`

(12) United States Patent
Makriyannis et al.

(10) Patent No.: US 8,293,211 B2
(45) Date of Patent: Oct. 23, 2012

(54) CB1 RECEPTOR ANTAGONISTS AND USES THEREOF

(75) Inventors: Alexandros Makriyannis, Watertown, MA (US); Venkata K Vemuri, Boston, MA (US)

(73) Assignee: MAKScientific, LLC, Mystic, CT (US)

( * ) Notice: Subject to any disclaimer, the term of this patent is extended or adjusted under 35 U.S.C. 154(b) by 0 days.

(21) Appl. No.: 12/157,578

(22) Filed: Jun. 11, 2008

(65) Prior Publication Data
US 2009/0035219 A1 Feb. 5, 2009

Related U.S. Application Data

(60) Provisional application No. 60/943,122, filed on Jun. 11, 2007.

(51) Int. Cl.
*A61K 49/00* (2006.01)
*A61K 31/5377* (2006.01)
*A61K 31/454* (2006.01)
(52) U.S. Cl. ................ 424/9.1; 514/236.5; 514/326
(58) Field of Classification Search .................. 514/406, 514/236.5, 237.2, 326, 330
See application file for complete search history.

(56) References Cited

U.S. PATENT DOCUMENTS
2010/0063050 A1* 3/2010 Makriyannis et al. ...... 514/236.5

FOREIGN PATENT DOCUMENTS
WO WO 2006074445 A2 * 7/2006

OTHER PUBLICATIONS

Wikipedia, Inborn errors of metabolism, 2010.*
Jbilo et al. The FASEB Journal, p. 1-27, published online Jul. 11, 2005.*
Joseph Tam et al., Peripheral CB1 Cannabinoid Receptor Blockade Improves Cardiometabolic Risk in Mouse Models of Obesity, The Journal of Clinical Investigation, Aug. 2010, pp. 2953-2966, vol. 120, No. 8.
Helge Frieling et al., Elevated Cannabinoid 1 Receptor mRNA is linked to Eating Disorder Related Behavior and Attitudes in Females With Eating Disorders, Psychoneuroendocrinology, 2009, pp. 620-624, vol. 34.
Charles W. Schindler et al., Effects of Cannabinoid Receptor Antagonists on Maintenance and Reinstatement of Methamphetamine Self-Administration in Rhesus Monkeys, European Journal of Pharmacology, 2010, pp. 44-49, vol. 633.
Sara J. Ward et al., The CB1 Antagonist Rimonabant (SR141716) Blocks Cue-Induced Reinstatement of Cocaine Seeking and other Context and Extinction Phenomena Predictive of Relapse, Drug and Alcohol Dependence, 2009, pp. 248-255, vol. 105.
Deanna L. Kelly et al., Effects of the Cannabinoid-1 Receptor Antagonist Rimonabant on Psychiatric Symptoms in Overweight People With Schizophrenia, Journal of Clinical Psychopharmacology, Feb. 2011, pp. 86-91, vol. 31, No. 1.
Mark D. Black et al., AVE1625, a Cannabinoid CB1 Receptor Antagonist, as a Co-Treatment With Antipsychotics for Schizophrenia: Improvement in Cognitive Function and Reduction of Antipsychotic-Side Effects in Rodents, Psychopharmacology, 2010, pp. 1-15.
Herling, Andreas W. et al. "CB1 receptor antagonist AVE1625 affects primarily metabolic parameters independently of reduced food intake in Wistar rats", Am J Physiol Endocrinol Metab 293:E826-E832, 2007.
MERIDIA (sibutramine hydrochloride monohydrate) Medication Guide.
Lange, Jos H.M. et al. "Synthesis, Biological Properties, and Molecular Modeling Investigations of Novel 3,4-Diarylpyrazolines as Potent and Selective CB1 Cannabinoid Receptor Antagonists", J. Med. Chem. 2004, 47, 627-643.
Rinaldi-Carmona, Murielle et al. "SR147778 [5-(4-Bromophenyl)-1-(2,4-dichlorophenyl)-4-ethyl-N-(1-piperidinyl)-1H-pyrazole-3-carboxamide], a New Potent and Selective Antagonist of the CB1 Cannabinoid Receptor: Biochemical and Pharmacological Characterization", The Journal of Pharmacology and Experimental Therapeutics, vol. 310, No. 3, JPET 310:905-914, 2004.
XENICAL (orlistat) Medication Guide.
Griffith, David A. et al. "Discovery of 1-[9-(4-Chlorophenyl)-8-(2-chlorophenyl)-9H-purin-6-yl]-4-ethylaminopiperidine-4-carboxylic Acid Amide Hydrochloride (CP-945,598), a Novel, Potent, and Selective Cannabinoid Type 1 Receptor Antagonist", J. Med. Chem. 2009, 52, 234-237.
Witkamp, Renger F. "Current and Future Drug Targets in Weight Management", Pharm Res (2011) 28:1792-1818 DOI 10.1007/s11095-010-0341-1, Published online: Dec. 23, 2010.
Rinaldi-Carmona, Murielle et al. "Biochemical and Pharmacological Characterisation of SR141716A, the First Potent and Selective Brain Cannabinoid Receptor Antagonist", Life Sciences, vol. 56, Nos. 13/24, pp. 1941-1947, 1995.
Armstrong, Helen E. et al. "Substituted acyclic sulfonamides as human cannabinoid-1 receptor inverse agonists", Bioorganic & Medicinal Chemistry Letters 17 (2007) 2184-2187.

* cited by examiner

*Primary Examiner* — Yong Chu
(74) *Attorney, Agent, or Firm* — Alix, Yale & Ristas, LLP

(57) ABSTRACT

Neutral antagonists of the CB1 cannabinoid receptor, means for identifying neutral antagonists of the CB1 cannabinoid receptor, and uses thereof. Antagonists of the CB1 cannabinoid receptor can be used to prevent, treat or reduce the severity of various medical conditions and symptoms, including, but not limited to obesity, appetite disorder, another metabolic disorder, drug addiction and/or mental illness. Administering neutral CB1 cannabinoid receptor antagonists in place of or in combination with known CB1 cannabinoid receptor antagonists or inverse CB1 cannabinoid receptor agonists in an individual or animal to treat a medical condition with a reduction of unwanted side effects. A method of detecting a neutral CB1 cannabinoid receptor antagonist, including identifying a candidate compound; subjecting the candidate compound to one or more of a cAMP assay, CB1 competitive binding assay, food intake assay, thermoregulation assay, or emesis assay; and selecting the compound if it exhibits neutral antagonist activity.

15 Claims, 11 Drawing Sheets

Compound 1

Compound 2

Compound 3

CB1 RECEPTOR ANTAGONISTS AND USES THEREOF

RELATED APPLICATION

This application claims priority under 35 U.S.C. 119(e) from U.S. Provisional Application No. 60/943,122 filed Jun. 11, 2007 for "CB1 Receptor Antagonists and Uses Thereof", the entire disclosure of which is hereby incorporated by reference.

FIELD

This disclosure generally relates to antagonists of the cannabinoid (CB)1 G-protein coupled receptor (CB1), particularly certain neutral antagonists. Such compounds have a range of useful applications including use to treat certain medical conditions with no or substantially reduced incidence of side-effects.

SUMMARY

There are reports that the endogenous cannabinoid system includes cannabinoid (CB)1- and CB2 G-protein coupled receptors (GPCRs). Activity at cannabinoid receptors is said to decrease adenylyl cyclase and the conversion of adenosine triphosphate (APT) to cyclic adenosine 3'5'-monophosphate (cAMP). CB1 receptors have been reported to be localized throughout the central nervous system including the brainstem, hypothalamus, and reward centers of humans and rodents. In the periphery, CB1 receptors are said to be found in the gut adipocytes and other tissues.

There is recognition that the anatomical location of CB1 receptors corresponds to many known behavioral and physiological effects of cannabinoid receptor agonists and inverse agonists. Many investigations suggest that the endogenous cannabinoid system plays a role in the modulation of food intake and related metabolic processes. There are reports that at least certain cannabinoid agonists increase food intake when given centrally or peripherally. Fasting is thought by some to increase endocannabinoid levels in the brain and small intestine of rodents.

There are reports that the CB1 receptor inverse agonist SR141716A (Acomplia®/Rimonabant) can achieve significant reductions in body weight, and have improved lipid and glycaemic profiles.

Unfortunately, there have been reports of drawbacks associated with the use of agents that can modulate the CB1 receptor. Many relate to the appearance of unwanted side-effects when the agents are used in mammals. The magnitude of the side-effects is said to range from very unpleasant (vomiting) to potentially life-threatening (anxiety).

For instance, there are reports that under some conditions, activation of CB1 receptors can lead to nausea and emesis. In humans, the antiemetic effect of marijuana ($\Delta^9$-tetrahydrocannabinol) is often used to counter the noxious effect of radiation and chemotherapy. CB1 receptor inverse agonists have been reported to have the opposite effect. In animal models of emesis, SR141716A (Acomplia®/Rimonabant) and a related compound (N-(Piperidin-1-yl)-5-(4-iodophenyl)-1-(2,4-dichlorophenyl)-4-methyl-1H-pyrazole-3-carboxamide (referred to herein as Compound 1; see FIG. 12)) potentiate vomiting induced by emetic stimuli. In rats, high doses of Compound 1 and SR141716A (Acomplia®/Rimonabant) can produce sickness behaviors and conditioned taste aversion (CTA). In overweight and obese humans treated with SR141716A (Acomplia®/Rimonabant) a small but significant number of patients have reported experiencing nausea. The appearance of these and other noxious side-effects has hindered more widespread use of these agents, particularly in susceptible populations.

Some compounds, for example Compound 1 and SR141716A (Acomplia®/Rimonabant), may be "inverse agonists". These agents are said to inhibit spontaneous or intrinsic activity by the CB1 receptor in certain in vitro systems. The phenomenon can be monitored by increased adenylyl cyclase and cAMP expression in treated cell lines expressing the CB1 receptor.

Some compounds may be "neutral antagonists". These agents are said to have no effect on intrinsic receptor activity at least in certain test systems. However, these agents may be able to block receptor binding and activation, usually by a competitive agonist.

It would be desirable to have antagonists that exhibit essentially no CB1 receptor activity and which block or significantly reduce receptor activation by a suitable agonist. It would be further desirable to have neutral antagonists of the CB1 receptor that can be used to prevent, treat, or reduce the severity of symptoms of certain medical conditions. It would be especially desirable to have neutral antagonists that exhibit no or minimal side-effects in vivo.

The present disclosure generally relates to antagonists of the cannabinoid (CB)1 G-protein coupled receptor (CB1), and particularly to certain neutral antagonists. The disclosure has a wide range of uses including use in treatment of certain medical conditions with no or substantially reduced incidence of noxious side-effects. The disclosure also relates to methods for reducing side-effects associated with use of the known CB1 receptor antagonists such SR141716A (Acomplia®/Rimonabant). Screens to detect new neutral antagonists are also disclosed.

Provided herein are chemically specific and biologically significant heteropyrole congeners of N-(Piperidin-1-yl)-5-(4-iodophenyl)-1-(2,4-dichlorophenyl)-4-methyl-1H-pyrazole-3-carboxamide (Compound 1) that antagonize the CB1 receptor as determined by assays disclosed herein. In one aspect, the disclosure provides a neutral antagonist having the chemical structure of Compound 3 (See FIG. 12) and physiologically acceptable salts and derivatives thereof.

In another aspect, the disclosure provides chemically specific and biologically significant heteropyrrole congeners of Compound 1 that antagonize the CB1 receptor. In one aspect, there is provided a neutral antagonist having the chemical structure of Compound 2 (See FIG. 12) and physiologically acceptable salts and derivatives thereof.

In another aspect, the disclosure provides a method of modulating (increasing or decreasing) CB1 receptor binding and activation in an individual or an animal without substantially modulating activity of the receptor. In one embodiment, the method includes administering to the individual or animal a therapeutically effective amount of at least one of the neutral antagonists disclosed herein, particularly at least one of Compound 2, Compound 3, as well as physiologically acceptable salts and derivatives thereof.

Also provided by the present disclosure is a method to treat, prevent, or reduce the severity of a condition in an animal or individual having that condition. In one embodiment, the method includes administering to the individual or animal in need of same a therapeutically effective amount of at least one of the neutral antagonists disclosed herein, particularly at least one of Compound 2, Compound 3, as well as physiologically acceptable salts and derivatives thereof.

Further provided by the disclosure is a method to treat, prevent, or reduce the severity of a condition in an animal or individual having that condition.

In one embodiment, the method includes administering to the individual or animal in need of same a therapeutically effective amount of a known CB1 receptor antagonist (e.g., SR141716A (Acomplia®/Rimonabant)) in combination with at least one of the neutral antagonists disclosed herein, particularly at least one of Compound 2, Compound 3, and/or physiologically acceptable salts and derivatives thereof.

In another aspect, the disclosure provides a method for reducing unwanted side-effects associated with administration of known CB1 receptor antagonists such as SR141716A (Acomplia®/Rimonabant) or other inverse CB1 agonists to certain individuals. In one embodiment, the method includes administering a therapeutically effective amount of at least one of the neutral antagonists disclosed herein, particularly at least one of Compound 2, Compound 3, or physiologically acceptable salts and derivatives thereof. In a related embodiment, the method further includes reducing the dose of the CB1 receptor antagonist (e.g., SR141716A (Acomplia®/Rimonabant)) or other inverse CB1 agonists to help spare the individual from unwanted side-effects.

The disclosure further provides a method to detect candidate compounds with significant neutral antagonist activity. In one embodiment, the method includes at least one of and preferably all of the following steps:

(1) identifying an agonist, antagonist, inverse agonist, partial agonist, or partial antagonist of the CB1 receptor (the "candidate compound"), (2) subjecting the candidate compound to at least one of a:
a) suitable cAMP assay,
b) suitable CB1 competitive binding assay,
c) suitable food intake assay and lever pressing behavior,
d) suitable thermoregulation assay,
e) suitable emesis assay and/or taste reactivity study; and (3) selecting the candidate compound if it has neutral antagonist activity.

Further uses and advantages of the disclosure are discussed, infra.

In general, unless otherwise explicitly stated the disclosed methods, articles and materials may be alternately formulated to comprise, consist of, or consist essentially of, any appropriate steps or components herein disclosed. The disclosed methods, articles and materials may additionally, or alternatively, be formulated so as to be devoid, or substantially free, of any steps, components, materials, ingredients, adjuvants or species used in the prior art or that are otherwise not necessary to the achievement of the function of the present disclosure.

When the word "about" is used herein it is meant that the amount or condition it modifies can vary some beyond that so long as the advantages of the disclosure are realized. The skilled artisan understands that there is seldom time to fully explore the extent of any area and expects that the disclosed results might extend, at least somewhat, beyond one or more of the disclosed limits. Later, having the benefit of this disclosure and understanding the concept and embodiments disclosed herein, a person of ordinary skill can, without inventive effort, explore beyond the disclosed limits and, when embodiments are found to be without any unexpected characteristics, those embodiments are within the meaning of the term about as used herein. It is not difficult for the artisan or others to determine whether such an embodiment is either as expected or, because of either a break in the continuity of results or one or more features that are significantly better than reported in this disclosure, is surprising and thus an unobvious teaching leading to a further advance in the art.

DETAILED DESCRIPTION

Figures 1A, 1B, 1C:
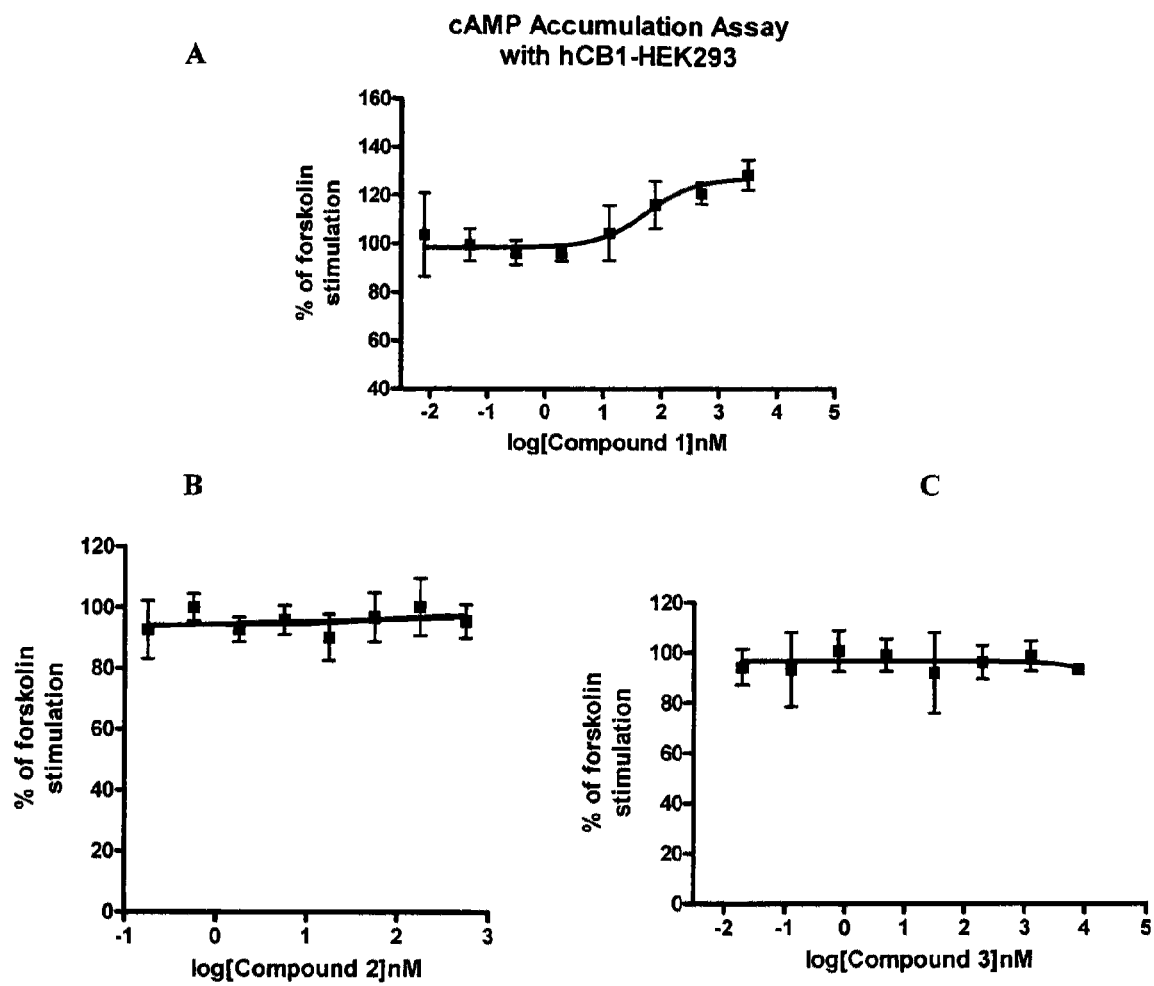
FIGS. 1A-1C are graphs showing cAMP accumulation with hCB1-HEK292 cells for Compounds 1, 2 and 3.

As discussed, the disclosure relates to antagonists of the cannabinoid (CB)1 G-protein coupled receptor (CB1), particularly certain neutral antagonists. Further provided are uses of such neutral antagonists including use to treat, prevent or reduce the symptoms of certain medical conditions.

As also discussed, the disclosure provides a neutral antagonist having the chemical structure of Compound 2 (See FIG. 12) and physiologically acceptable salts and derivatives thereof. Further provided is a neutral antagonist having the chemical structure of Compound 3 (See FIG. 12) and physiologically acceptable salts and derivatives thereof.

By the phrase "neutral antagonist" is meant a compound that has little or no detectable intrinsic CB1 receptor activity and that has capacity to block or reduce receptor binding and activation by a competitive agonist. See Pertwee, R. G. (2005) Life Sci. 76: 1307 for more information.

By "physiologically acceptable salts" is meant salts typically useful for pharmaceutical applications including acid addition salts and basic salts. Examples of acid addition salts are hydrochloride salts, hydrobromide salts, methane sulfonate salts, etc. Examples of basic salts are salts where the cation is selected from alkali metals, such as sodium and potassium, alkaline earth metals, such as calcium, and ammonium ions. Other examples of physiologically acceptable salts can be found in "Remington's Pharmaceutical Sciences" 17. Ed. Alfonso R. Gennaro (Ed.), Mark Publishing Company, Easton, Pa., U.S.A., 1985 and more recent editions, and in Encyclopedia of Pharmaceutical Technology.

Reference herein to a "derivative of Compound 2", "derivative of Compound 3", as well as like phrases, is meant a heteropyrrole congener with about the same molecular weight as Compound 2 or Compound 3 (e.g., an isomer) which congener exhibits at least one of and preferably all of the following characteristics: (1) essentially no forskolin-stimulated cAMP accumulation (i.e., less than about 5%, 4%, 3%, 2%, 1% cAMP accumulation) in the standard forskolin-stimulated cAMP assay (defined below); (2) between about 10 to about 1000 fold selectivity for the CB1 receptor verses the CB2 receptor, preferably about 20, 50, 100, 200 or 500 fold selectivity in what is referred to herein as the standard CB1 binding assay (defined below); (3) provide for about a 10% to about 70% reduction in food intake and/or weight loss in what is referred to herein as the standard food intake assay (defined below), for instance, a 20%, 30%, 40%, 50%, or 60% reduction in food intake and/or weight loss; (4) shows essentially no increase in vomiting and/or gaping according to the standard emesis test (defined below). Specifically excluded from the definition of "derivative" is Compound 1 and SR141716A (Acomplia®/Rimonabant).

As mentioned, the disclosure provides for a method of modulating CB1 receptor binding and activation in an individual or an animal without substantially modulating activity of the receptor. Particular methods involve administering to the individual or animal a therapeutically effective amount of at least one of the neutral antagonists disclosed herein including physiologically acceptable salts and derivatives thereof. Modulation of CB1 receptor binding and activation can be detected and optionally quantified by one or a combination of strategies known in the field. A useful assay is disclosed by US Pat. Application No. 2006/0100208 to Makriyannis et al., for instance, at paragraphs [0299] to [0301]; including references disclosed therein. By "modulation" is meant capacity to increase or decrease CB1 receptor binding and activation relative to a suitable control.

By the phrase "without substantially modifying activity of the CB1 receptor" and like phrases is meant less than about 15%, 10%, 5%, 4%, 3%, 2%, 1% activation relative to a suitable control.

A suitable CB2 receptor binding assay for use with the present invention is disclosed by US Pat. Application No. 2006/0100208 to Makriyannis et al., for instance, at paragraph [0302]; including references disclosed therein.

As used herein a "therapeutically effective amount" of a compound, is the quantity of a compound which, when administered to an individual or animal, results in a sufficiently high level of that compound in the individual or animal to cause a physiological response. The inventive compounds described herein, and physiologically acceptable salts and derivatives thereof, have pharmacological properties when administered in therapeutically effective amounts for providing a physiological response useful to treat, prevent or reduce the severity of medical conditions referred to herein, particularly obesity, appetite disorders, lifestyle choices such as a desire to lose weight, cardiovascular disorders, metabolic disorders such as diabetes, lipid metabolic disorders such as elevated LDL, elevated cholesterol, and low HDL, improvement in lipid profiles and insulin related deficiencies, addiction to cannabis, nicotine, cocaine, opiates and other drugs of abuse, enhancement of cognition and memory, and mental disorders including schizophrenia. Typically, a "therapeutically effective amount" of an inventive compound is believed to range from about 10 mg/day to about 1,000 mg/day.

As used herein, an "individual" refers to a human. An "animal" refers to, for example, veterinary animals, such as dogs, cats, horses and the like, and farm animals, such as cows, pigs and the like.

Compounds of the invention can be administered by a variety of known methods, including orally, rectally, or by parenteral routes, (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular, subcutaneous, ocular, intranasal, inhalation-based and transdermal administration) and slow releasing microcarriers (for rectal, intramuscular or intravenous administration). The formulations can also contain a physiologically acceptable excipient, vehicle and optional adjuvants, flavorings, colorants and preservatives. Suitable physiologically acceptable vehicles include, for example, saline, sterile water, Ringer's solution and isotonic sodium chloride solutions. The specific dosage level of active ingredient will depend upon a number of factors, including, for example, biological activity of the particular preparation, age, body weight, sex and general health of the individual being treated.

Figure 12:
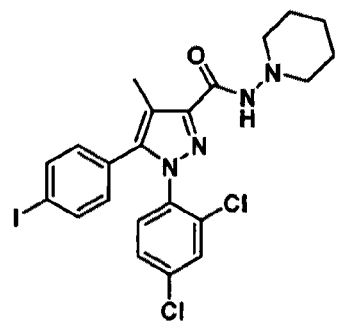
FIG. 12 is a drawing showing the chemical structures of Compounds 1, 2 and 3. Compounds 2 and 3 are considered neutral antagonists according to the invention.
Figure 12:
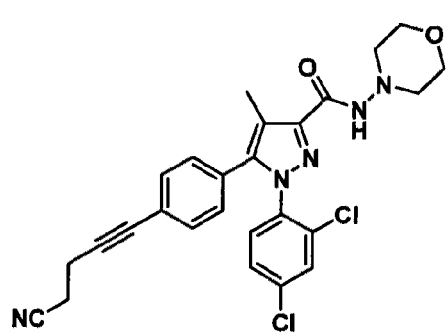
Figure 12:
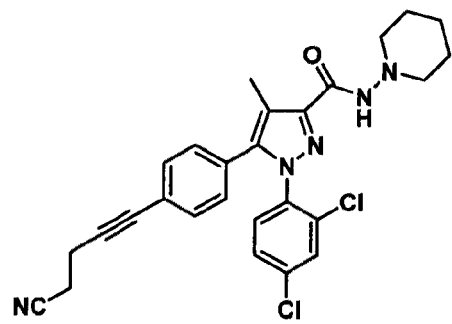

By "compound of the disclosure" is meant the specific neutral antagonists shown in FIG. 12 (i.e., Compounds 2 and 3) as well as those physiologically acceptable salts and derivatives thereof disclosed herein.

Accordingly, it is an object to treat, prevent or reduce the severity of an individual suffering from or susceptible to obesity or an appetite disorder or other metabolic disorders, such as diabetes, lipid metabolic disorders such as elevated LDL, elevated cholesterol, and low HDL, drug addiction, mental disorders including schizophrenia and other cognition and memory deficits by administering a therapeutically effective amount of at least one compound of the invention. Related methods can be used to provide weight loss in individuals who have made a lifestyle choice to lose weight i.e., the extra weight is not immediately health threatening.

As will be apparent, the compounds of the invention can be used alone or in combination with other CB1 receptor antagonists known to the field. Examples of such agents include Xenical® (Orlistat), Meridia® (Sibutramine), Phentermine, SR147778 (Surinabant), AVE-1625, CP-945,598 (Otenabant), MK-0364 (Taranabant), SLV-319 (Ibipinabant), V24343 and SR141716A (Acomplia®/Rimonabant). In one embodiment, less than five compounds of the disclosure, preferably one or two of same is used in combination with less than five of the known CB1 antagonists, preferably one or two of same.

There are reports that use of SR141716A (Acomplia®/Rimonabant) in at least some individuals is associated with unwanted side-effects. These include nausea, dizziness, diarrhea, and anxiety (all determined by recognized testing procedures), depression and suicidal tendencies. In embodiments in which a neutral antagonist of the disclosure is used in combination with SR141716A (Acomplia®/Rimonabant) or other CB1 antagonists, it will be possible to reduce or even eliminate one or more of these side-effects, particularly nausea. That is, it is possible to reduce the amount of Rimonabant SR141716A (Acomplia®/Rimonabant) or other CB1 antagonists administered to the individual who has had, is receiving or is about to receive a therapeutically effective amount of one or more neutral antagonists of the disclosure. In one embodiment, the amount of SR141716A (Acomplia®/Rimonabant) administered to the individual is reduced by 1.5 to 5-fold compared to the accepted therapeutic amount. The individual is then dosed with a therapeutically effective amount of at least one of the compounds of the disclosure. Of course, it is also possible to increase the length of time between doses of SR141716A (Acomplia®/Rimonabant) with the same or similar effect.

Accordingly, one embodiment provides for a method for reducing unwanted side-effects (one or more of nausea, dizziness, diarrhea, and anxiety) typically associated with administration of SR141716A (Acomplia®/Rimonabant) or other CB1 antagonists to certain individuals. A particular method involves administering a therapeutically effective amount of at least one of the compounds of the disclosure so as to reduce the side-effects in that individual. As discussed, the method can involve reducing the amount of SR141716A (Acomplia®/Rimonabant) or other CB1 antagonists administered to the individual.

Compounds of the disclosure can be administered before, during or after administration of any one of Xenical® (Orlistat), Meridia® (Sibutramine), Phentermine, SR147778 (Surinabant), AVE-1625, CP-945,598 (Otenabant), MK-0364 (Taranabant), SLV-319 (Ibipinabant), V24343 and SR141716A (Acomplia®/Rimonabant), as needed by the user or medical practitioner, so long as intended results are achieved.

Further provided is a method for selecting a compound that has significant neutral antagonist activity. In one embodiment, the method includes at least one of, and preferably all, of the following steps:
(1) identifying a candidate compound thought to be a neutral antagonist (e.g., an agonist, antagonist, inverse agonist, partial agonist, or partial antagonist of the CB1 receptor), (2) subjecting the candidate compound to at least one of a:

a) suitable cAMP assay such as the standard forskolin-stimulated cAMP assay referred to in Example 2, b) suitable CB1 competitive binding assay such as the standard CB1 binding assay referred to in Example 4 (if desired, a suitable CB2 receptor binding assay for determining CB1/CB2 receptor affinity has been disclosed above and in Example 3), c) suitable food intake assay such as the standard food intake assay referred to in Example 6 and example 10, and operant lever pressing behavior as in example 11, d) suitable thermoregulation assay such as the in vivo assay disclosed in Example 7, e) suitable emesis assay such as the standard emesis test mentioned in Example 8 and/or taste reactivity paradigm as in example 9; and (3) selecting that candidate compound having neutral antagonist activity.

As will be apparent from the present disclosure, it will be possible to select useful neutral antagonists by one or a combination of strategies. In one embodiment, and with respect to assay (a), the candidate compound provides essentially no change (i.e. less than about 15%, 10%, 5%, 4%, 3%, 2%, or 1%) in cAMP levels in the assay when compared to a suitable control such as Compound 1. In another embodiment, and with respect to assay (b), the candidate compound binds the CB1 receptor in the CB1 competitive binding assay and exhibits a CB1 receptor/CB2 receptor binding ratio of between from about 10 to about 1000 fold, for instance, about 20, 50, 100, 200 or about 500 fold. Radiolabeled CP55,940 may be used as a control. In another embodiment, and with respect to assay (c), the candidate compound provides for between from about a 10% to about 70% decrease in food intake, for instance, about 20%, 30%, 40%, 50%, about 60%, compared to a suitable control such as vehicle or Compound 1. In another embodiment, and with respect to assay (c), the candidate compound provides for between from about 10% to about 70% decrease in body weight, for instance, about 20%, 30%, 40%, 50%, 60%, compared to a suitable control such as vehicle or Compound 1. Particular candidate compounds will, with respect to assay (d), essentially block (i.e., less than about 5%, 4%, 3%, 2%, or about 1%) the hypothermic effect of a suitable CB1 agonist (e.g., CP55,940) compared to a suitable control such as vehicle. With respect to assay (e), particular candidate compounds will not substantially increase the number of vomiting and/or gaping episodes when compared to a suitable control such as Compound 1 (combined with an emetic such as M6G). Preferred candidate compounds will, when compared to Compound 1, have less than about 50%, 40%, 30%, 20%, 10% or about 5% gape frequency in the assay provided for in (e). In one embodiment the neutral antagonist candidate compound will provide neutral antagonist activity with respect to a plurality or all of the assays.

The following examples are given for purposes of illustration only in order that the present disclosure may be more fully understood. These examples are not intended to limit in any way the scope of the disclosure unless otherwise specifically indicated.

Example 1

Compound Synthesis and Formulation

Compound 3 is a pyrazole congener of Compound 1 ((N-(Piperidin-1-yl)-5-(4-iodophenyl)-1-(2,4-dichlorophenyl)-4-methyl-1H-pyrazole-3-carboxamide). See FIG. 12 (showing the chemical structure of Compound 2 and Compound 3). For information, see US Pat. Publ. No. 2006/0030563, US Pat. Publ. No. 2006/0192667, US Pat. Publ. No. 2006/0100208, U.S. Pat. Pub. No. 2004/0192667, U.S. Pat. No. 7,119,108; and references disclosed therein. See also Mclaughlin, P. et al. (2005). Psychopharmacology (Berl) 180: 286-293, 36. Lan, R. et al. (1999) J. Med. Chem. 42: 769-776. Chambers, A P et al. (2006) Br. J. Pharmacol. 147: 109-116, and Mclaughlin, P. et al. (2003) Behav. Pharmacol. 14: 583-588 as well as references cited therein. CP55,940((−)-cis-3-[2-Hydroxy-4-(1,1dimethylheptyl)phenyl]-trans-4-(3-hydroxypropyl)cyclohexanol; Tocris Cookson Inc., Ellisville, Mo., U.S.A.), and M6G (morphine-6-glucoronide; Lipomed Inc., Switzerland) were dissolved in dimethyl sulfoxide (DMSO) using gentle sonication before being diluted with Tween 80 and saline (4% DMSO; 1% Tween 80; 95% saline).

Example 2

Forskolin-Stimulated cAMP Assay

Intracellular cAMP levels were measured with a competitive protein-binding assay using intact HEK293 cells expressing hCB1 or hCB2 and a cAMP immunoassay kit from Sigma (St. Louis, Mo.). In short, forskolin stimulated cells were incubated with various concentrations of compound, cAMP anti-body and cAMP conjugate for 2 hours at ambient temperature. The reaction was stopped by emptying the wells followed by the addition of p-NPP substrate and incubation for 1 hour. This reaction was stopped and absorbance intensity, detected at 405 nm, was inversely proportional to the concentration of cAMP produced by the cells. The results were expressed as percent inhibition of forskolin-stimulated cAMP accumulation and EC50 curves were generated with the use of GraphPad Prism software.

Compound 3 did not change the forskolin-stimulated cAMP accumulation in CB1 transfected HEK cells up to concentrations of 630 nM (FIG. 1) and is therefore considered to be a CB1 neutral antagonist. Previously published results have shown that the inverse agonist, Compound 1, increases forskolin stimulated cAMP with an EC50 of 363.8 nM1.

FIG. 1 shows cAMP data for Compound 2 and Compound 3 and is explained in more detail as follows. Compound 2 and Compound 3 are neutral antagonists, as they have no effect on forskolin stimulated cAMP production after binding to human CB1 receptors. The results are from one assay done in triplicate.

Reference herein to a "standard forskolin-stimulated cAMP assay" or like phrase refers to the foregoing assay method.

Example 3

[$^3$H]CP55,940 Competitive Binding Assay

Compounds were tested for their CB1 and CB2 receptor using membrane preparations from rat brain or HEK293 cells expressing hCB2 receptor, respectively, and [$^3$H]CP55,940 as previously described 1, 36-38. Stock solutions of the compounds (10 mM in DMSO) were diluted in TME buffer (50 mM Tris-HCL, 3 mM MgCl$_2$, 100 mM NaCl, 0.2 mM EDTA, pH 7.4) with 0.1% BSA and transferred to 96 well plates containing [$^3$H]CP55,940 (specific activity 128 Ci/mmol; NIDA) at a final concentration of 0.76 nM. Non-specific binding was assessed in the presence of 100 nM CP55,940. The binding reaction was initiated with the addition of the respective membrane suspension (~50 µg membrane protein) followed by incubation at 30° C. with gentle agitation in a shaking water bath for 60 minutes. Binding was terminated by rapid filtration of the membrane suspension over Unifilter GF/B-96 Well Filter Plates (Packard Instruments) using a Packard Filtermate-196 Cell Harvester. The filter plates were washed with ice-cold wash buffer (50 mM Tris-base, 5 mM MgCl$_2$ with 0.5% BSA) and bound radioactivity was determined using a Packard TopCount Scintillation Counter. The results were analyzed using nonlinear regression to determine the actual IC50 and the Ki values of the ligand (Prizm by GraphPad Software, Inc.). All data were in duplicate with IC50 and Ki values determined from at least two independent experiments.

Example 4

CB1/CB2 Affinity

The affinity of a compound for CB1 vs. CB2 is determined by the ratio of the inhibitory constants (Ki), as determined by the competitive binding assay.

Figure 2A:
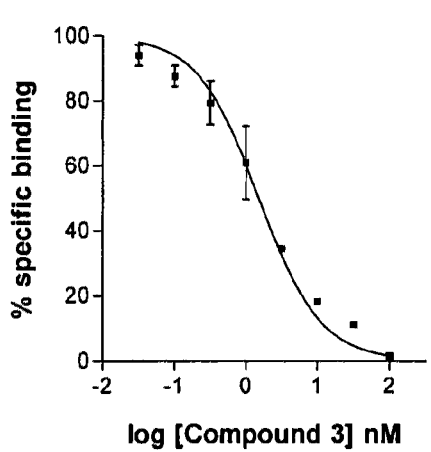
FIGS. 2A-2B are graphs showing CB1 and CB2 receptor binding for Compound 3.
Figure 2B:
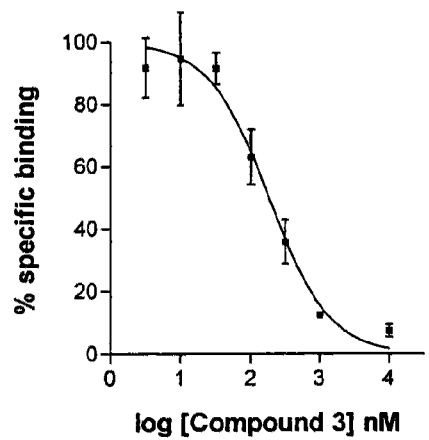

In competitive receptor binding assays against [$^3$H]CP55, 940, Compound 3 shows selectivity for the CB1 receptor compared to CB2. As shown in FIG. 2, Compound 3 binds to cannabinoid receptors with a CB1 Ki of 0.89 nM and a CB2 Ki of 92 nM.

Compound 3 binds to CB1 receptors with high affinity, exhibiting 100-fold selectivity for CB1 versus CB2 receptors. Previously published results have demonstrated that the inverse agonist Compound 1 is 430 times more selective for CB1 than CB2.

Referring now to FIG. 2, the figure shows binding data for Compound 3. Values for Ki are in nM±standard deviation of seven (CB1) or two (CB2) assays done in duplicate.

Reference herein to a "standard CB1 binding assay" or like phrase refers to the CB1 competitive binding assay mentioned in this example.

Example 5

Behavioral Experiments

All experimental protocols were approved by internal guidelines. Different concentrations of drugs were administered I.P. in a 1 ml kg-1 (milliliters per kilogram) volume, except M6G, which was given s.c. (subcutaneously) in a 0.1 ml kg-1 volume.

Example 6

Food Intake Studies

Male Sprague-Dawley (SD) rats weighing between 330-380 g at the start of the study were used to compare the effects of the neutral antagonist Compound 3 (5 mg kg-1 or milligrams per kilogram) and inverse agonist Compound 1 (5 mg kg-1) on short term food intake and body weight. Animals were fed strawberry flavored Ensure Plus® liquid diet (53.3% carbohydrate, 29% fat, and 16.7% protein; 1.41 kcal g-1) (Abbott Laboratories, Abbott Park, Ill., U.S.A), and habituated to testing and handling procedures, daily, for seven days prior to testing. Food and water were presented in inverted glass bottles that attached to the outside of the cage. Food was available for 18 h each day starting at 16:00 h (12 h light-dark cycle; lights off 16:00 h).

Experiment A

Given that Compounds 1 and 3 have similar molecular weights and similar binding affinities, it was decided to compare the effect of 5 mg kg-1 of each compound on food intake. This dose was chosen based on an assumption that 5 mg kg-1 is a highly anorectic dose of Compound 1. The day before the experiment rats were assigned to one of three treatment groups; vehicle [mean bodyweight±standard error of the mean (SEM); 354±5 g, n=6], Compound 1 (354±4 g, n=6), or Compound 3 (352±11 g, n=6). At 15:30 rats were weighed and injected with either vehicle, Compound 3 (5 mg kg-1) or Compound 1 (5 mg kg-1). Intake measurements were taken at 1.5 h, 3 h, 5 h, and 18 h after food became available.

Experiment B

In a second study we examined the effect of Compound 3 (1 mg kg-1; 5 mg kg-1) on food intake and body weight in rats treated daily with the compound for 5 days. Rats were habituated to testing and handling procedures as before. The day before the experiment rats were assigned to one of three treatment groups; vehicle (363±10 g, n=5), Compound 3 1 mg kg-1 (365±5 g, n=5), Compound 3 5 mg kg-1 (361±9 g, n=5). Food intake and body weight were monitored daily.

Experiment C

In a third study, the acute effect of two additional doses of Compound 3 (10 mg kg-1; 20 mg kg-1) on food intake and body weight were assessed in rats from the first two experiments. Vehicle and Compound 1 (5 mg kg-1) treated rats were again used for comparison. Following a two week washout, rats were assigned to one of four treatment groups; vehicle (492±8 g, n=6), Compound 1 5 mg kg-1 (496±11 g, n=6), Compound 3 10 mg kg-1 (491±7 g, n=6), or Compound 3 20 mg kg-1 (489±9 g, n=6). On the day of the experiment each rat received only a single injection, 30 min later food was made available as described in experiment 1. Food intake was measured 0.5, 1.5, 3, 5, and 18 h after administration. Food intake and body weight were monitored daily for five days after the experiment to assess the sustained effect of a single administration of each compound.

Figure 3A:
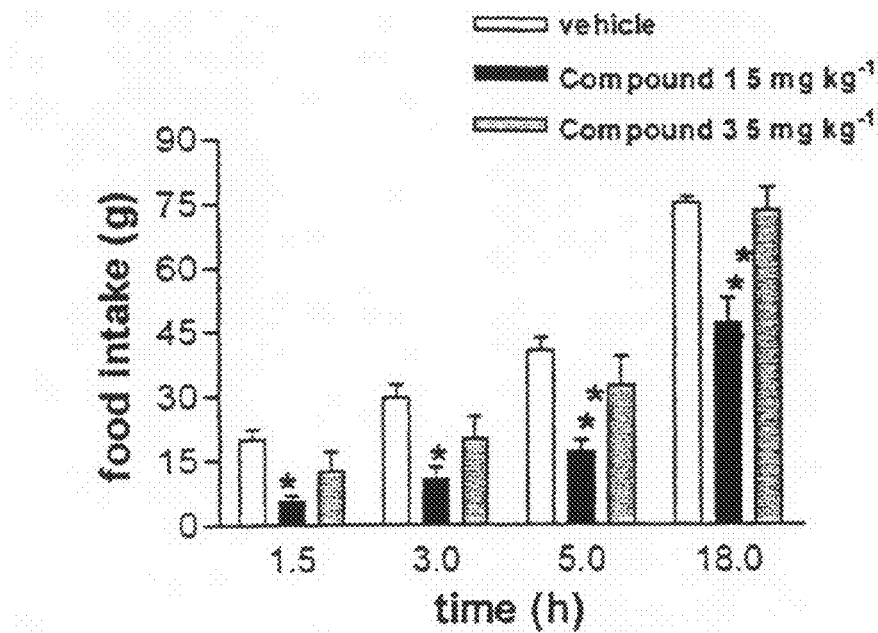
FIGS. 3A-3C are graphs showing food intake (3A, 3B) and body weight (3C) following administration of Compound 1 or Compound 3 to rats.

In experiment A, above, the anorectic effect of the neutral CB1 receptor antagonist Compound 3 (5 mg kg-1) was examined. Vehicle treated rats and rats treated with the inverse agonist Compound 1 (5 mg kg-1) were used for comparison (FIG. 3a). A 2-way ANOVA performed on the food intake data showed a significant treatment×time interaction (F(6,15)=3.5, P<0.01). The inverse agonist Compound 1 significantly reduced food intake at each time point relative to vehicle treated rats 21,40; mean difference; 1.5 h (−14.3 g), 3 h (−19.0 g), 5 h (−23.5 g), 18 h (−28.0 g), P<0.05, Newman-Keuls Multiple Comparison Test. Rats treated with Compound 1 also ate significantly less than rats treated with the neutral antagonist Compound 3 at 5 h (−15.5 g) and 18 h (−26.1 g) time points, P<0.05. Compound 3 did not significantly reduced food intake compared with vehicle treated rats at the 5 mg kg-1 dose, P>0.05.

Figure 3B:
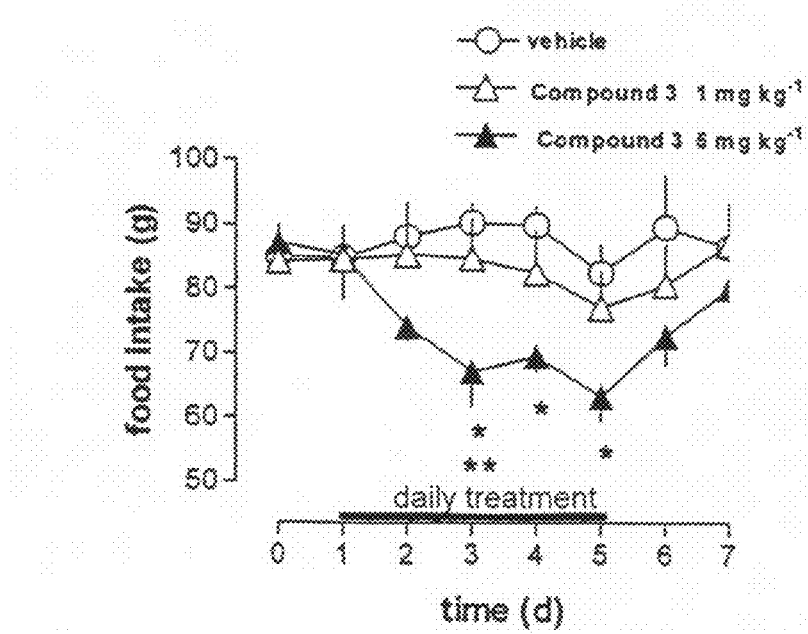

In experiment B, above, it was of interest to learn how daily treatment with Compound 3 (1 mg kg-1; 5 mg kg-1) effected food intake over five days (FIG. 3b). A 2-way ANOVA performed on the food intake data showed that there was a significant treatment by time interaction, F(10,12)=3.1, P<0.005. No significant reductions in food intake were observed in rats treated with the neutral antagonist Compound 3 (1 mg kg-1; 5 mg kg-1) on the first day of treatment, F(2,12)=0.0, P=0.99. Differences in food intake were not statistically significant on the second day of treatment either, F(2,12)=2.4, P=0.12. However, subsequent treatments did produce significant reductions in food intake at the 5 mg kg-1 dose compared with vehicle treated rats on day 3 (−23.2 g), day 4 (−20.4 g), and day 5 (−19.2 g), P<0.05, Newman-Keuls Multiple Comparison Test. There was also a significant effect of dose, F(2,10)=3.6, P<0.001. Differences between the 1 mg kg-1 and 5 mg kg-1 doses were significant on treatment day 3 (−17.6 g), P<0.05.

Reductions in food intake by the 5 mg kg-1 dose of Compound 3 were accompanied by significant reductions in weight gain (FIG. 3c); 2-way ANOVA (effect of time) F(9, 12)=148.7, P<0.001. Rats treated with 5 mg kg-1 of the neutral antagonist Compound 3 gained significantly less weight than rats treated with 1 mg kg-1 of Compound 3 on day 4 (−12.0 g), P<0.05, and significantly less weight than vehicle treated rats on day 4 (−15.6 g), day 5 (−21.8 g), and day 6 (−23.7 g). Although rats treated daily with the 1 mg kg-1 dose of Compound 3 tended to eat less, and gain less weight, than vehicle treated rats such differences were non significant, P>0.05. The results demonstrate that repeated administrations of a 5 mg kg-1 dose of the neutral antagonist Compound 3 significantly reduced food intake and weight gain in rat.

Figure 3C:
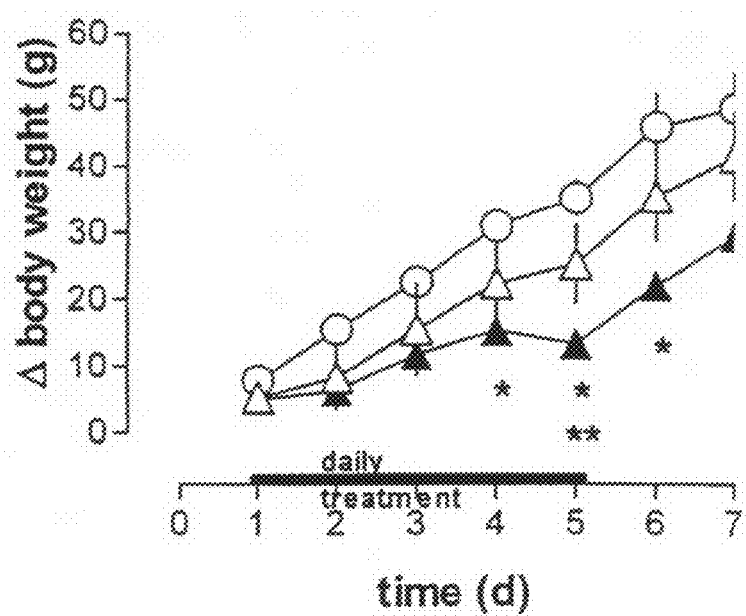

FIGS. 3A-3C show the effect of Compound 1 and Compound 3 on food intake and are explained in more detail as follows.

FIG. 3A. A highly anorectic dose of Compound 1 (5 mg kg-1, n=5) significantly reduced food intake (mean±SEM; g) compared with vehicle (n=5) treated rats, or rats treated with the neutral CB1 receptor antagonist Compound 3 (n=5), p<0.05, Newman-Keuls Multiple Comparison Test. *=significantly different than vehicle treatment, **=significantly different than treatment with Compound 3. In this experiment, Compound 3 (5 mg kg-1) failed to significantly effect food intake.

FIG. 3B. In a second experiment, the effect of 5 daily treatments with the neutral antagonist Compound 3 (1; 5 mg kg-1, n=5/5) on food intake was examined. At the 5 mg kg-1 dose, Compound 3 significantly reduced food intake after the third day of treatment, P<0.05.

FIG. 3C. Weight gain in rats treated daily with either vehicle or Compound 3 (1; 5 mg kg-1). Weight gain was significantly reduced in rats treated with the 5 mg kg-1 dose of the neutral antagonist Compound 3, P<0.05, *=significantly different than vehicle, **=significantly different than 1 mg kg-1

Figure 4A:
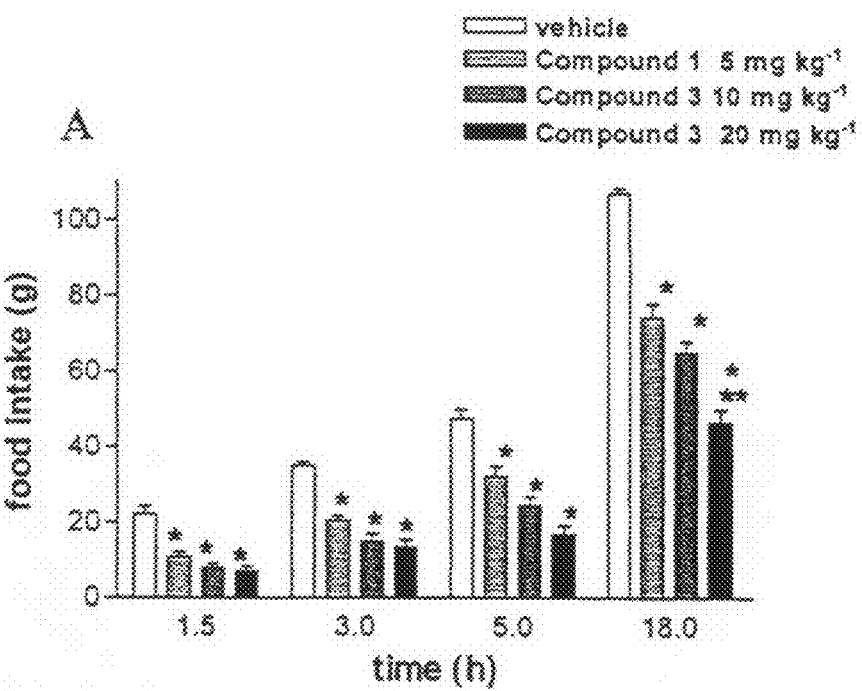
FIGS. 4A-4C are graphs showing food intake (4A, 4B) and body weight (4C) following administration of Compound 1 or Compound 3 to rats.
Figure 4B:
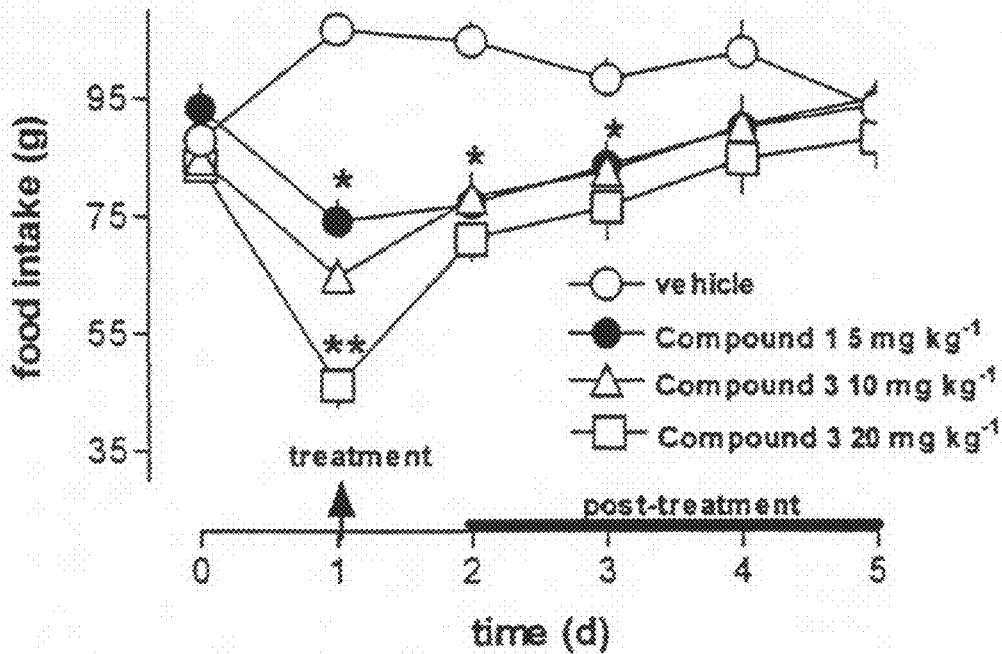

In experiment C, the acute effect of Compound 3 on food intake was re-examined by evaluating two additional doses of the neutral antagonist (10; 20 mg kgl). Vehicle and Compound 1 treated rats were used for comparison. FIG. 4a shows the early effect of Compound 3 and Compound 1 on food intake. Results from a 2-way ANOVA performed on the data revealed a significant treatment by time interaction, $F(9,20)=18.1$, P<0.0001. As expected, Compound 1 significantly reduced food intake at each time point, P<0.05. Food intake was also reduced in rats treated with the neutral CB1 receptor antagonist Compound 3 (10; 20 mg kg-1) compared with vehicle treated rats; 1.5 h (−14.3 g, −15.0 g), 3 h (−20.0 g, −21.3 g), 5 h (−22.8 g, −30.1 g), and 18 h (−42.0 g, −60.6 g), P<0.05. Differences in food intake between 10 and 20 mg kg-1 treatment groups were significant at the 18 h time point, P<0.001. Differences between rats treated with Compound 1 and Compound 3 were significant at 3, 5, and 18 h time points, P<0.05. The results demonstrate that the neutral receptor antagonist Compound 3 produced early, and dose-dependent, reductions in food intake in rat. Furthermore, the anorectic effect of the neutral antagonist Compound 3 (10 mg kg-1; 20 mg kg-1) was sustained for several days after the experiment. FIG. 4B shows the mean daily food intake in each group before and after treatment. A 2-way ANOVA performed on the daily food intake data revealed a significant treatment× time interaction, $F(15,20)=12.7$, P<0.0001. Differences in food intake between groups were non significant prior to treatment, $F(3,20)=1.5$, P=0.22. After treatment, food intake was reduced in rats treated with Compound 1 or Compound 3 relative to vehicle treated rats, P<0.05. The sustained effect of an acute administration of Compound 1 has been reported previously by our group 21,40. Here we report reductions in food intake by the neutral antagonist Compound 3 were similar in duration to anorectic effect of the inverse agonist Compound 1.

Figure 4C:
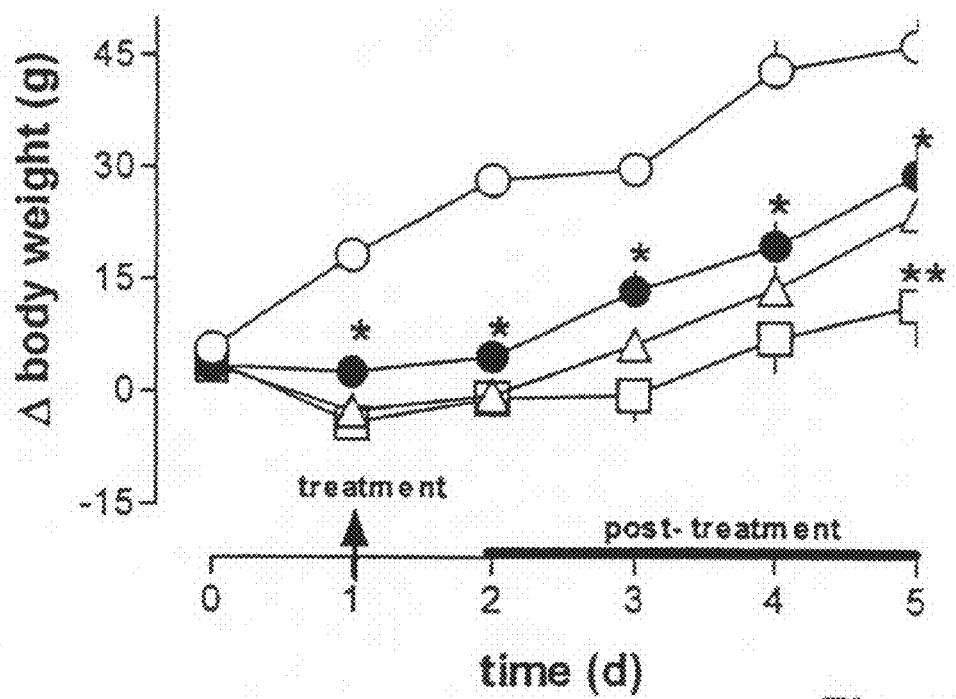

FIG. 4C shows that reductions in food intake by Compound 1 and the neutral antagonist Compound 3 (10; 20 mg kg-1) were also associated with significant reductions in weight gain over time, compared with vehicle treated rats. Results from a 2-way ANOVA performed on the data showed that there was a significant treatment×time interaction, $F(15, 20)=10.9$, P<0.0001. Weight gain was significantly reduced in rats treated with either Compound 1 or Compound 3 for several days after the experiment; P<0.05, Newman-Keuls Multiple Comparisons Test. A 2-way ANOVA performed on the weight change data also showed a significant effect of dose, $F(3,20)=27.9$, P<0.0001. Differences in weight gain between 10 mg kg-1 and 20 mg kg-1 Compound 3 treatment groups were significant on day 5 (−12.3 g), P<0.05. The results demonstrate that a single administration of the neutral antagonist Compound 3 (10 mg kg-1; 20 mg kg-1) produced a sustained reduction on weight gain in addition to food intake.

FIGS. 4A-4C show the effect of 2 additional doses of Compound 3 (10 mg kg-1; 20 mg kg-1, n=6/6) on food intake and weight gain were compared with vehicle treated rats (n=6) or rats treated with the inverse agonist Compound 1 (n=6) and are explained in more detail as follows.

FIG. 4A. At higher doses, Compound 3 significantly reduced food intake, P<0.05, Newman-Keuls Multiple Comparison Test.

FIGS. 4B-4C. Daily food intake (mean±SEM; g) and cumulative weight change (mean±SEM; g) are shown before and after the experiment. Both the inverse agonist Compound 1 and neutral antagonist Compound 3 significantly reduced food intake and weight gain for several days after treatment, P<0.05. *=significantly different than vehicle, **=significantly different than 10 mg kg-1 Compound 3.

Reference herein to a "standard food intake assay" will mean the test referred to in Experiment B, above.

Example 7

In vivo Antagonism By Compound 3 at CB1 Receptors: Thermoregulation Assay

To determine whether Compound 3 antagonized CB1 receptors in vivo, we examined hypothermia induced by the CB1 agonist CP55,940 (0.3 mg kg-1) 42 in rats pre-treated with either vehicle, Compound 1 (5 mg kg-1, n=5) 40, or Compound 3 (5 mg kg-1, n=5) 45 min earlier at 14:45 h. Briefly, silicone coated temperature data loggers (SubCue Inc, Calgary, Canada) were surgically implanted into the abdominal cavity of male SD (450-500 g) rats under isoflurane anesthesia (4% induction; 2-2.5% maintenance). Rats were allowed to recover for 3 days before being acclimatized to testing and handling procedures for an additional seven days. Core body temperature readings were sampled every 5 min for 300 min during the course of each experiment.

Figures 5A, 5B:
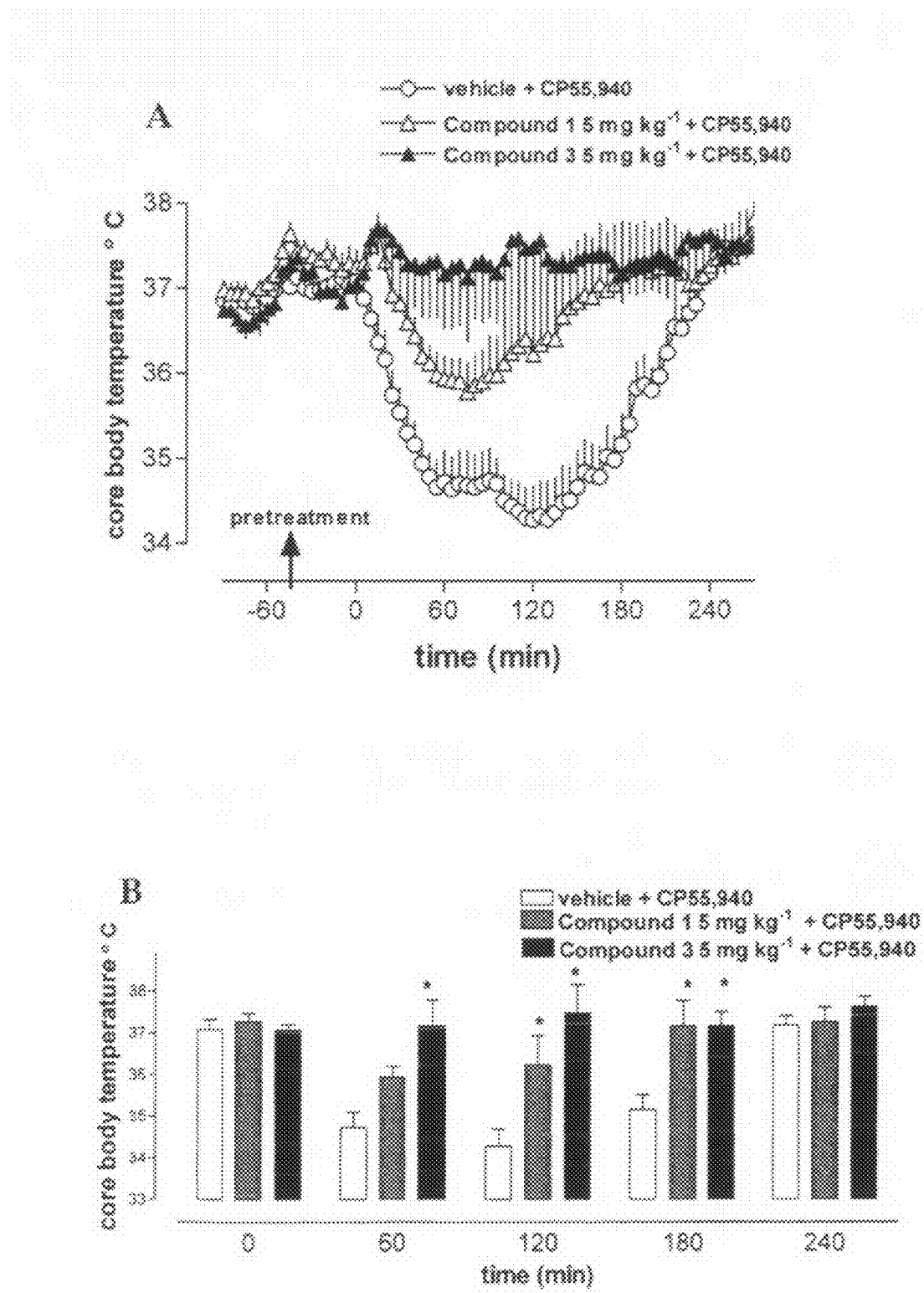
FIGS. 5A-5B are graphs showing core body temperature following administration of Compound 1 or Compound 3 to rats.

FIG. 5A shows changes in body temperature over time. A 2-Way ANOVA performed on the body temperature data showed a significant treatment×time interaction, $F(144,12)=4.4$, P<0.0001. Differences between vehicle, Compound 1, and Compound 3 treated rats were analyzed using a 1-way ANOVA at selected time points (FIG. 5B). Prior to treatment, differences in body temperature between treatment groups was non significant, time 0, $F(2,14)=1.02$, P=0.72. As expected, body temperature rapidly fell in vehicle treated rats after the administration of the CB1 agonist CP55, 940. In comparison, the hypothermic effect of CP55,940 was significantly attenuated in rats pre-treated with inverse agonist Compound 1, and completely blocked in rats treated with the neutral antagonist Compound 3, compared with vehicle treated rats, P<0.05, Newman-Keuls Multiple Comparisons Test.

FIGS. 5A-5B are each explained in more detail as follows.

FIG. 5A. Body temperature (mean temp ° C.±SEM) in rats pretreated with either vehicle (n=5), Compound 1 (5 mg kg-1, n=5), or Compound 3 (5 mg kg-1; n=5), followed by treatment with the CB1 agonist CP55,940 (0.3 mg kg-1) at time 0.

FIG. 5B. The neutral antagonist Compound 3 (5 mg kg-1, n=5) and inverse agonist Compound 1 (5 mg kg-1, n=5) both block hypothermia induced by CP 55, 940, P<0.05, Newman-Keuls Multiple Comparison Test. The results demonstrate that Compound 3 and Compound 1 effectively antagonizes CB1 receptors in vivo. Note that Compound 3 was more effective than Compound 1 at antagonizing the hypothermic effect of CP55,940.

Example 8

Emesis Studies

Four studies were conducted in four groups of adult male ferrets (900-1500 g) in order to examine how Compound 3 and Compound 1 effect emesis. In the first study, ferrets received either the neutral antagonist Compound 3 (5 mg kg-1; I.P., n=5) or vehicle 15 min before the emetic M6G (0.05 mg kg-1; s.c.) 30. Ferrets were lightly anaesthetized with halothane for each injection. Data were videotaped and analyzed by an observer blinded to the conditions of each treatment group. During 60 min of observation the number of vomiting (emetic) episodes were counted, and activity or sleeping time was noted. The second and third study were the same as the first except that higher doses of Compound 3 (10 mg kg-1; 20 mg kg-1; I.P., n=4) were used. In the fourth study the inverse agonist Compound 1 (5 mg kg-1, n=5) was used instead of the neutral antagonist Compound 3. Each ferret acted as its own control, conditions were randomized via a counter balance design and separated by at least 14 days.

Figure 6:
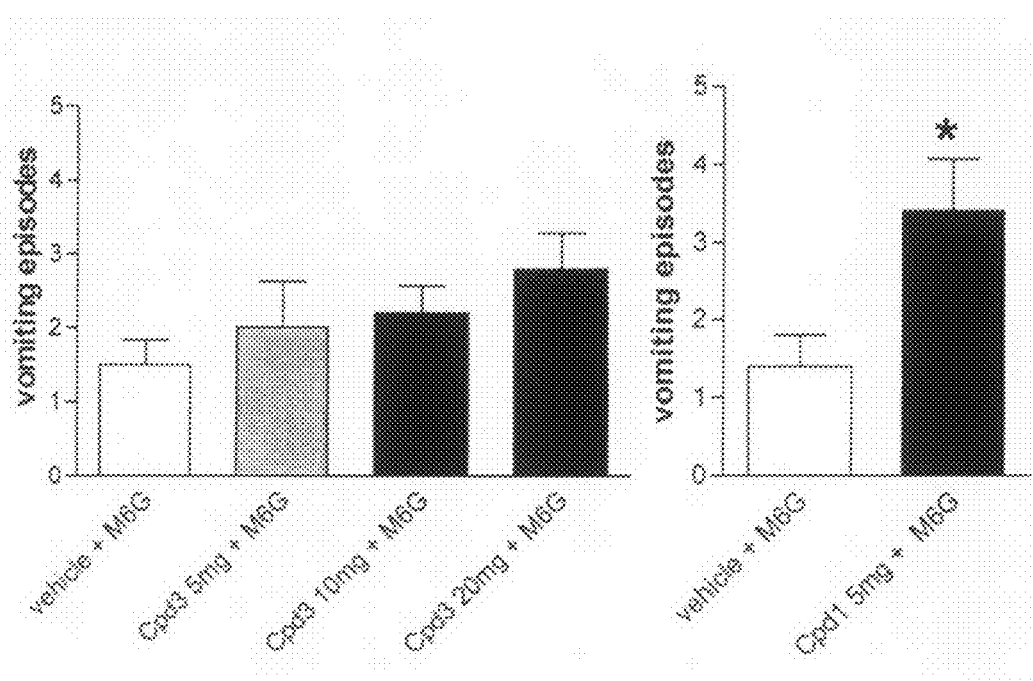
FIG. 6 is a graph showing vomiting episodes (emesis) following administration of Compound 1 or Compound 3.

To compare the potentially adverse effect of the neutral antagonist Compound 3 with Compound 1, it was of interest to see how each compound effected emesis induced by the emetic M6G (FIG. 6). The neutral antagonist Compound 3 (5 mg kg-1; mg kg-1) did not significantly increase the number of vomiting episodes compared with vehicle conditions, even at doses that significantly reduce food intake (mean number of vomiting episodes±SEM); vehicle 1.2±0.2 vs. 5 mg kg-1 2.0±0.6, P>0.05; vehicle 1.0±0.4 vs. 10 mg kg-1 2.0±0.4, P>0.05 vehicle 1.5±0.8 vs. 20 mg kg-1 2.7±0.6, P>0.05. In comparison, pre-treatment with the inverse agonist Compound 1 potentiated the number of vomiting episodes induced by M6G; vehicle 1.4±0.4 vs. Compound 13.4±0.6, P<0.05, two-tailed paired t-test.

Reference herein to a "standard emesis test" refers to the vomiting assay mentioned in this example.

FIG. 6 shows emesis in ferrets pretreated with either vehicle, Compound 1 (5 mg kg-1, n=5), or Compound 3 (5 mg kg-1; 10 mg kg-1; 20 mg kg-1, n=5/4) followed by the emetic M6G (0.5 mg kg-1) and is explained in more detail as follows. Compound 1 potentiated the emetic effect (mean number of vomiting episodes±SEM) of M6G in ferret, P<0.05 (paired t-test). In comparison, three doses of Compound 3 failed to significantly effect emesis. Note that the neutral antagonist Compound 3 had no effect on emesis at doses that significantly reduced food intake (FIG. 4) and blocked CP 55, 940 induced hypothermia (FIG. 5).

Example 9

Taste Reactivity Studies

Rats were implanted with intraoral cannulae and 24 hrs prior to the surgical procedure, they were administered a prophylactic antibiotic (Derapin, 100 mg/kg, sc; Ayerst). On the day of surgery, the rats were anaesthetized with isofluorane gas and were administered Anafen (7.0 mg/kg, sc; Merial), a nonsteroidal anti-inflammatory drug (NSAID) with analgesic properties. A 3.0 $cm^2$ patch of fur was shaved at the back of the neck just above the scapula and the area was surgically prepared [Betadine surgical scrub (Purdue Frederick) and alcohol]. A thin-walled 15-gauge stainless steel needle was inserted at the back of the neck, directed s.c., around the ear and brought out behind the first molar inside the mouth. A length of IntraMedic polyetheylene tubing with an inner diameter of 0.86 mm and an outer diameter of 1.27 mm was then run through the needle after which the needle was removed. Two circular elastic discs were placed over the tubing and drawn to the exposed skin at the back of the neck for the purpose of stabilizing the cannula. The tubing was held secure in the oral cavity by an o-ring, which was sealed behind the tubing prior to cannulation surgery. For the purposes of conditioning and testing, the cannula was connected to the infusion pump (Harvard Apparatus, South Natick, Mass.) for delivery of the solution by slipping the tubing of the cannula inside a second polyethylene tube (inner diameter 1.19 mm, outer diameter 1.70 mm) attached to the infusion pump. Two rats were subsequently removed from the study due to an ineffective cannula.

Five days after surgery and prior to conditioning (day 1), rats were individually placed in the Plexiglas taste reactivity chamber (22.5×26×20 cm) with their cannula attached to the infusion pump for fluid delivery. The rats were habituated to the taste reactivity procedure by infusing them with water for a period of 5 min at a rate of 1.0 ml/min after which they were returned to their home cage. On day 2, the rats were individually taken to the chamber for a single conditioning trial. They were intraorally infused with 0.1% saccharin solution for 5 min at a rate of 1.0 ml/min while their orofacial and somatic responses were videotaped from a mirror at a 45° angle below the chamber. Immediately after the saccharin infusion the rats were injected with the appropriate dose of Compound 3, according to random assignment: 0.0 mg/kg (vehicle; n=8), 2.0 mg/kg (n=7), 4.0 mg/kg (n=7), 8.0 mg/kg (n=8). On day 5, the animals were given a second adaptation trial with a 5-min intraoral infusion of water.

Taste reactivity testing occurred on day 6, 96 hr after conditioning. The rats were taken to the chamber and following a period of 1 min were infused with 0.1% saccharin solution over a period of 5 min (1.0 ml/min) while being videotaped. Immediately after the session, the rats were returned to their home cage. On day 7, following 15 hr of water deprivation, the rats were given a 2-bottle preference test. The rats were presented with a graduated tube containing 0.1% saccharin solution and a graduated tube containing water for a period of 120 min. The amount consumed from each bottle during the 120 min of drinking was converted to a preference score: Amount consumed of saccharin solution/amount consumed of saccharin+amount consumed of water. The taste reactivity videotapes were scored using the Observer (Noldus Information Technology, Sterling, Va.) event-recording program. The behaviors scored included the frequency of gaping, chin rubs, ingestive reactions, passive drips and activity. Gaping was defined as rapid, large-amplitude opening of the mandible with retraction of the corners of the mouth. Chin rubbings were defined as chin or mouth in direct contact with the floor or wall of the chamber and forward projections of the body. Ingestive (hedonic) reactions were defined as the frequency of 2-s bouts of tongue protrusions (extensions of the tongue out of the mouth) and mouth movements (movement of the lower mandible without opening the mouth). The scores for tongue protrusions and mouth movements were summed to provide a total ingestive (hedonic) reaction score.

Figure 7A:
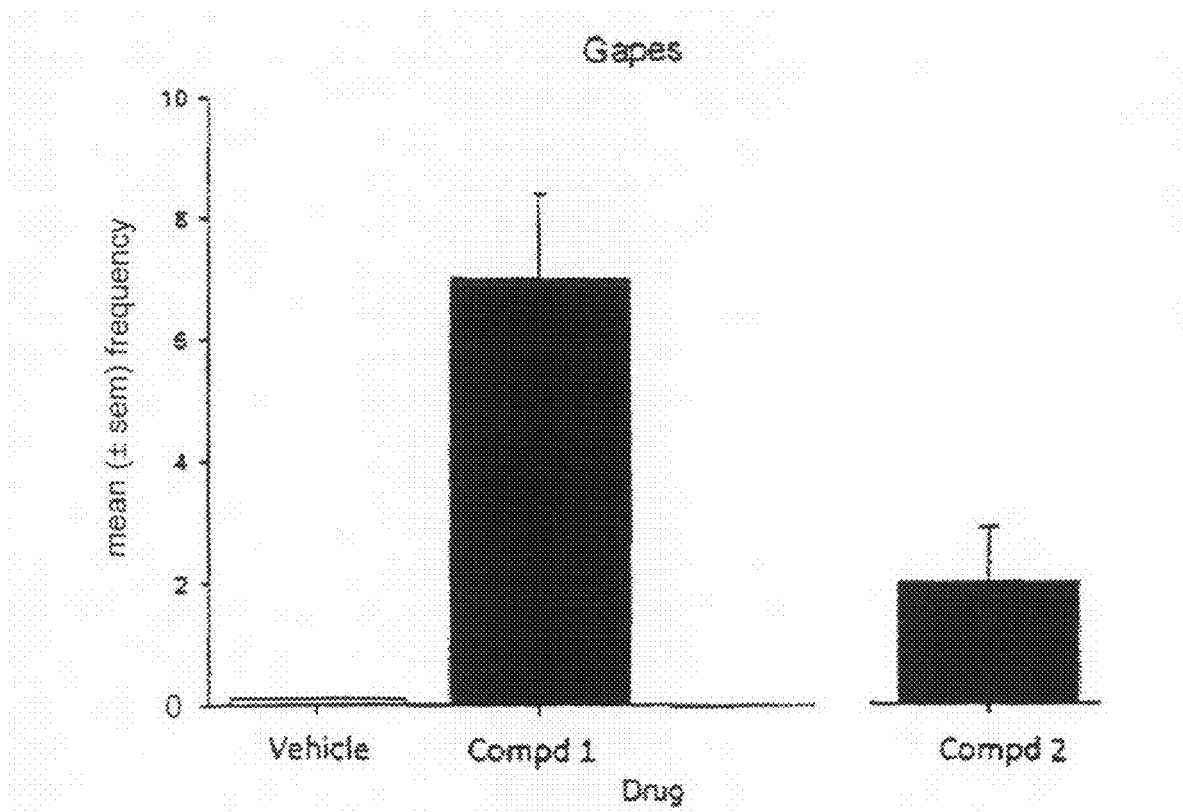
FIGS. 7A-7B show performance of conditioned gaping in the taste reactivity procedure using Compound 1, Compound 2 or Compound 3.
Figure 7B:
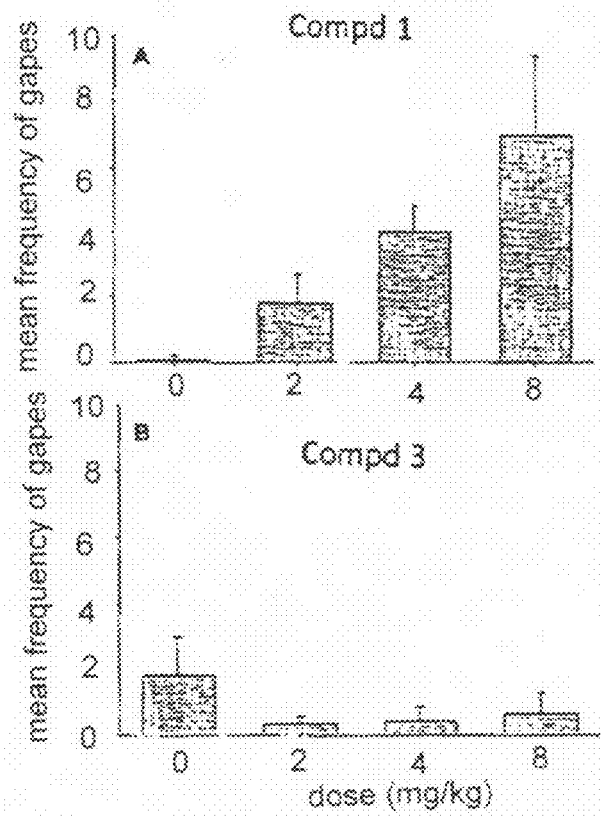

Compound 3 produced dose-dependent conditioned taste avoidance and suppression of ingestive (hedonic) taste reactivity scores, but it did not produce conditioned aversion as assessed by gaping and chin rubbing. Mean (±SEM) saccharin preference ratios were as follows: saline, 0.388 (+0.069), 2.0 mg/kg Compound 30.411 (0.059), 4.0 mg/kg Compound 30.298 (0.074), 8.0 mg/kg Compound 30.088 (+0.017). A single factor ANOVA of the saccharin preference ratio scores revealed a significant effect of dose (F (3, 26)=6.9; p<0.001); subsequent LSD pairwise comparisons revealed that at a dose of 8.0 mg/kg, Compound 3 produced conditioned avoidance of saccharin solution that differed significantly from all other groups (p<0.025). Compound 3 also produced conditioned suppression of ingestion (hedonic) taste reactions (Mean±SEM for each condition were as follows: saline, 9.0 (+3.2); 2.0 mg/kg Compound 3, 10.5 (3.2); 4.0 mg/kg Compound 3, 4.5 (1.5); 8.0 mg/kg Compound 3, 1.3 (0.5); F (3, 26)=3.2, p<0.05). Subsequent LSD pairwise comparison tests revealed that a dose of 8.0 mg/kg of Compound 3 produced significantly suppressed ingestion reactions relative to vehicle or 2.0 mg/kg of Compound 3 (p<0.05), but not 4.0 mg/kg of Compound 3. Despite these effects of Compound 3, there were no significant effects of Compound 3 on chin rubbing or conditioned gaping. FIG. 7 depicts the results with the conditioned gaping measure (FIG. 7B shows the effects of Compound 1 from McLaughlin et al. 2005b, while FIG. 5B displays the present results with Compound 3). Although Compound 1 has been shown to increase conditioned gaping, this effect was not seen with Compound 3. FIG. 7A shows the results for Compound 2 when compared to Compound 1.

Example 10

Food Intake Studies Using Different Diets

Animals were assigned to three different diet conditions (n=10/group). One group was assigned to a high-fat diet (HF; Diet # D12451, Research Diets, New Brunswick, N.J., 20% protein, 45% fat, 35% carbohydrate). A second group was given a high-carbohydrate diet (HC; Diet # D12450B, Research Diets, New Brunswick, N.J., 20% protein, 10% fat, 70% carbohydrate). The remaining group was fed a standard chow diet (LC, 5P00 Prolab RMH 3000, PMI Nutrition International, St. Louis, Mo.; 26% protein, 14% fat, 60% carbohydrate). Food blocks from each type of diet were nutritionally complete and similar in appearance and weight. Rats were given free access to lab chow in their home cages until the beginning of a five day habituation period. On the first day of habituation, rats were assigned to their respective dietary groups and moved into suspended wire mesh test cages containing their assigned food type. After spending 30 min in the test cage, they were returned to their home cages. After this initial habituation period, rats were given free access to lab chow in their home cages every Thursday afternoon through Monday afternoon. Each Tuesday and Wednesday, rats spent 30 min in the test cages with their assigned diets. On Thursdays, the injected animals were placed in the test cages with a pre-weighed amount of assigned food. A piece of cardboard was placed underneath the chamber to catch spillage. Following each session, all remaining food plus any spillage was collected and weighed. The difference between pre- and post-session food weights was considered to be the amount of intake. Rats in experiments 4 received IP injections of 2.0, 4.0, and 8.0 mg/kg doses of Compound 3. These rats received I.P. drug injections 30 min prior to the test session, and their doses were administered in randomized order using a repeated measures design.

Figure 8A:
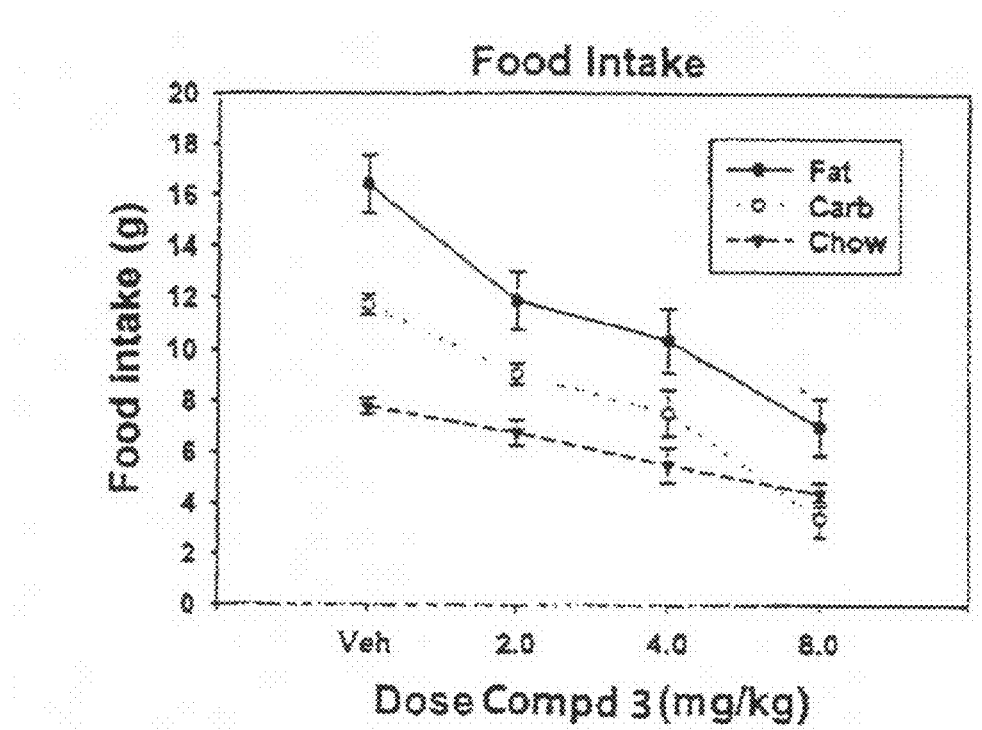
FIG. 8 shows the effect of Compound 3 on food intake of three different diets.
Figure 8B:
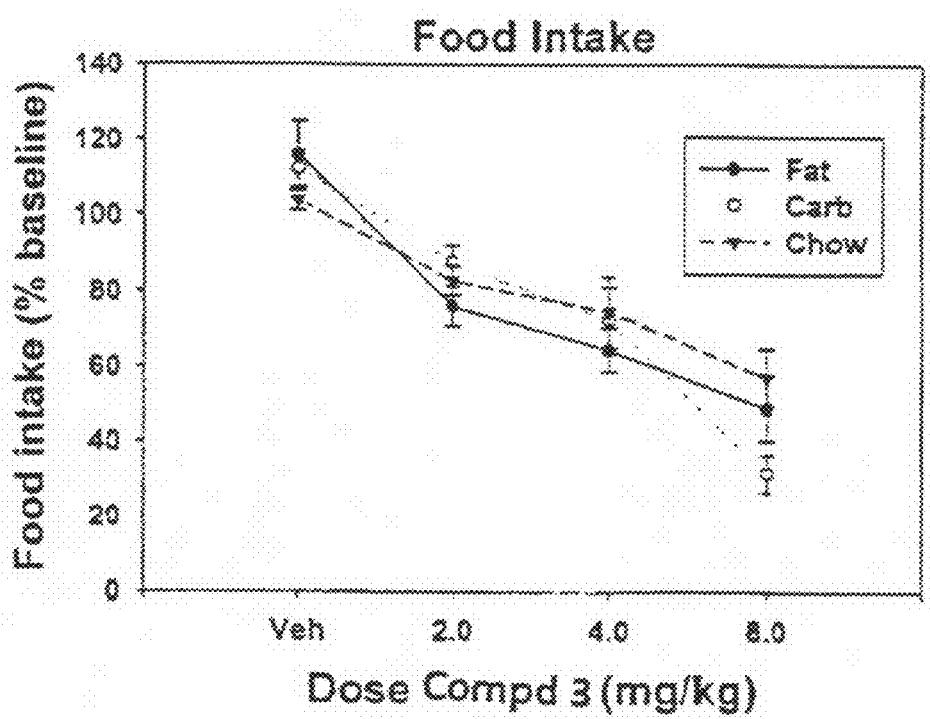

FIG. 8A depicts the effects of Compound 3 on food consumption. Compound 3 significantly suppressed food intake over vehicle across all diet groups ($F(3,81)=37.3$, $p<0.001$). Non-orthogonal planned comparisons show that every dose of Compound 3 significantly decreased consumption over vehicle. There was a significant effect of diet ($F(2,27)=49.82$, $p<0.001$), and there was a significant interaction between diet group and dose ($F(6,81)=3.44$, $p<0.005$). Separate analyses showed that intake of each of the three food types was significantly suppressed by Compound 3 ($p<0.01$). Moreover, the interaction effect disappeared when data were transformed to represent a percentage of baseline consumption, defined as the mean consumption of the previous two non-injection sessions ($F(6,81)=1.95$, NS; see FIG. 8B). There were no significant differences among the three dietary groups in the percent transformed data ($F(2,27)=0.18$, NS), but a robust drug treatment effect remained ($F(3,81)=54.08$, $p<0.001$).

Example 11

Operant Lever Pressing on $FR^5$ Schedules

Following the initial training period, rats (n=8 each group) were injected with drug and then tested once a week on Thursdays. For experiments 1 and 2, Compound 3 or Compound 2, respectively were injected IP at doses of 1.0, 2.0, 4.0, or 8.0 mg/kg or vehicle. Pretreatment time for these two experiments was 30 min. For experiments 3 and 4, rats were given drug or vehicle orally 1 hour before testing. In experiment 3, rats were given vehicle or 8.0, 16.0, or 32.0 mg/kg Compound 3. In experiment 4, rats received vehicle or Compound 2 at doses of 4.0, 8.0, or 16.0 mg/kg. All doses were given in a randomized order using a repeated measures design.

Figure 9:
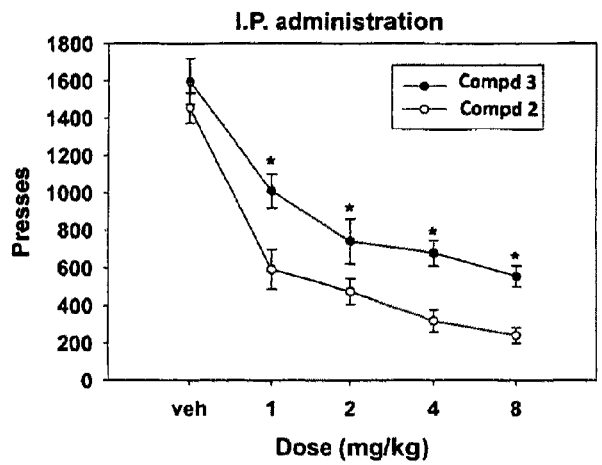
FIG. 9 shows the effects of I.P. (intraperitoneal) administered Compound 2 or Compound 3 on FR5 lever-pressing.

FIG. 9 (experiments 1 and 2) depicts the effects of IP administered Compound 3 and Compound 2 on $FR^5$ responding. Factorial ANOVA with repeated measures on dose revealed a significant overall effect of dose on lever pressing [$F(4, 56)=70.4$, $p<0.001$]. There were also significant differences between drug groups [$F(1,14)=16.8$, $p=0.001$], but no drug by dose interaction [$F(4, 56)=0.942$, n.s.]. Nonorthogonal planned comparisons revealed that every dose produced a significant decrease in lever pressing when compared to vehicle control ($p<0.05$), and separate analyses showed that both Compound 3 and Compound 2 significantly suppressed $FR^5$ responding compared to vehicle ($p<0.001$). The $ED_{50}$ for the effect on $FR^5$ responding was 0.78 mg/kg ($R^2=0.68$) for IP Compound 3, and 0.5763 mg/kg ($R^2=0.82$) for IP Compound 2.

Figure 10:
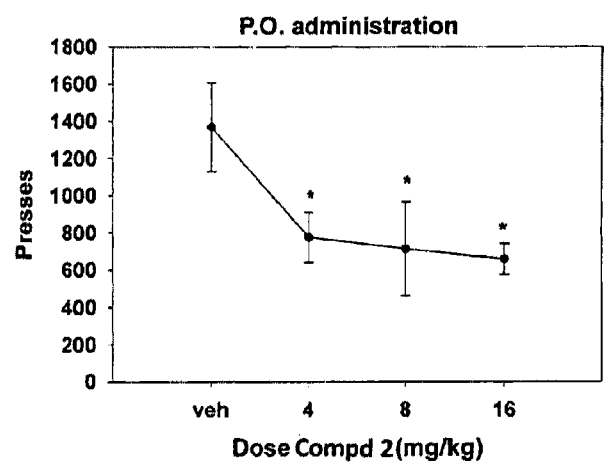
FIG. 10 shows the effect of orally administered (P.O) Compound 2 on FR5 lever pressing.
Figure 11:
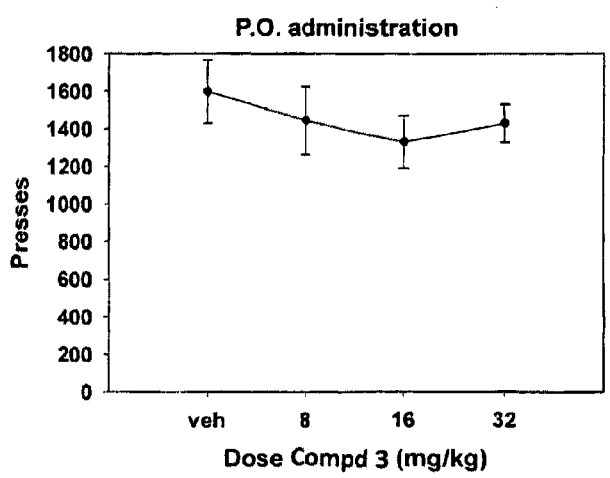
FIG. 11 shows the effect of oral administered (P.O.) Compound 3 on FR5 lever pressing

There was no significant change in lever pressing at any orally administered dose of Compound 3 when compared to vehicle [$F(3, 21)=0.522$, n.s.; FIG. 11]. However, oral Compound 2 produced a dose-dependent decrease in responding on $FR^5$ [$F(3, 21)=4.901$, $p=0.01$; FIG. 10]. Planned comparisons demonstrated that every dose of Compound 2 produced a significant suppression of responding compared to vehicle ($p<0.05$). The $ED_{50}$ of oral Compound 2 for suppression of lever pressing on $FR^5$ was 1.488 mg/kg ($R^2=0.3281$).

The following statistical methods were used as needed in the foregoing examples. Food intake and thermoregulation data were analyzed using a 2-way mixed design ANOVA with time as the repeated measure. Significant differences were followed up with 1-way independent measures ANOVA at each time point. Significant differences between treatments were further analyzed using Newman-Keuls multiple comparisons test. For the emesis data Paired t-tests (two tailed) were used to examine differences between vehicle, and antagonist or inverse agonist treated ferrets.

As shown and described above, the effects of the CB1 receptor neutral antagonist, Compound 2 and Compound 3 were compared against those of the inverse agonist Compound 1. Inverse agonist/antagonist properties were established in HEK293 cells transfected with human CB1 receptors. A forskolin stimulated cAMP assay was used to establish that this compound acted as a neutral antagonist in vitro in HEK cells transfected with human CB1 receptors. Forskolin stimulated cAMP production was significantly enhanced by the inverse agonist/antagonist Compound 1 in a concentration dependent manner, whereas, the pure antagonist Compound 3 had no effect on cAMP at any concentration. Compound 1 and Compound 3 displayed low Ki values in competitive binding assays with the CB1 agonist [H]3CP55,940, where Compound 3 showed approximately a 100-fold selectivity for CB1 over CB2 receptors. Both Compound 1 and Compound 3 significantly reduced food intake and weight gain in rat. Compared with Compound 1, higher doses of the neutral antagonist Compound 3 were needed to produce similar effects on food intake and weight gain. Despite this, Compound 3 antagonized the hypothermic effect of the CB1 receptor agonist CP55,940 more effectively than Compound 1 in a thermoregulation assay. It is significant that unlike Compound 1, Compound 3 did not significantly increase vomiting induced by the emetic M6G in ferret.

It was also of interest to see the impact of matching doses of each compound on food intake. Under the conditions described above, the neutral antagonist Compound 3 had no acute effect on food intake in rat at a 5 mg kg-1 dose. Whereas the same dose of the inverse agonist Compound 1 produced an immediate reduction in food intake that lasted several days. The sustained effect of Compound 1 on food intake has been reported previously by our group 21,40, and may result from the long half-life of this compound in rat (~22 h)41.

In a second experiment, rats were treated daily with 1 mg kg-1 and 5 mg kg-1 of the neutral antagonist Compound 3 for five days. These doses were chosen based on the efficacy with which the inverse agonist Compound 1 reduces food intake. Results from this experiment showed that rats treated with the neutral antagonist began to eat less than vehicle treated controls after the third day of treatment. Results from experiment 3 show that higher doses of Compound 3 produced an immediate reduction in food intake that persisted for several days after only a single injection. Reductions in food intake were accompanied by significant reductions in weight gain. The time course with which Compound 3 reduced food intake and body weight was similar to that seen with the inverse agonist Compound 1. Therefore, it is believed that Compound 3 appears to have a long half-live in vivo. The results clearly demonstrate that neutral antagonism alone at CB1 receptors inhibits food intake.

Potency with which each compound antagonized CB1 receptors directly using the CB1 receptor agonist CP55,940 was examined. Both the inverse agonist Compound 1 and the neutral antagonist Compound 3 significantly attenuated the hypothermia induced by CP55,940. However, overall Compound 3 was more effective than Compound 1 at blocking the effect of the CB1 agonist.

In addition, Compound 3 crosses the blood brain barrier within a short period after administration, because the hypothermic effect of cannabinoid agonists is specific to activity at CB1 receptors in the anterior hypothalamus. Compound 3 had no effect on forskolin stimulated cAMP production at any concentration. In comparison, cAMP production was significantly enhanced by Compound 1 in a concentration dependent manner. Compound 3 and Compound 1 displayed similar Ki values (Compound 3, 0.89±0.44 nM; Compound 14.78±0.15 nM 1 in competitive binding assays with the CB1/2 agonist [H]3CP55,940 where Compound 3 was 100-fold more selective for CB1 over CB2 receptors. Both Compound 1 (5 mg kg-1) and Compound 3 (1 mg kg-1; 5 mg kg-1; 10; 20 mg kg-1) significantly reduced food intake and weight gain in rat. Compared with Compound 1, higher doses of Compound 3 were needed to produce similar effects on food intake and weight gain. It was seen that Compound 3 and Compound 1 antagonized CB1 receptors in vivo by blocking hypothermia induced by CP55,940. Unlike Compound 1, Compound 3 did not significantly increase vomiting induced by the emetic morphine-6-glucoronide. The Examples show that a centrally active neutral CB1 receptor antagonist shares the appetite suppressant and weight loss affects of inverse agonists without potentiating emesis.

As discussed in more detail in the Examples above, inverse agonist/antagonist properties were established by measuring forskolin stimulated cAMP production in HEK293 cells transfected with human CB1/2 receptors using a non-radioactive competition immunoassay. Compound 3 CB1 receptor binding affinity was examined in competitive binding assays using the CB1 agonist [$^3$H] CP55,940. The effects of Compound 1 and Compound 3 on short term and long term food intake were examined in rats maintained on a high fat diet. In vivo antagonism of CB1 receptors by Compound 3 was confirmed using a thermoregulation assay that measured hypothermia induced by CP55,940. Lastly, the effect(s) of Compounds 1 and 3 on emesis were compared in ferrets treated with the emetic M6G.

It is believed that Compounds 2 and 3 as well as physiologically acceptable salts and derivatives thereof are neutral antagonists of the CB1 receptor. The compounds are believed to have similar or identical activities in at least one of the biological assays disclosed herein, particularly one or more of the standard forskolin-stimulated cAMP assay, standard CB1 binding assay, and the standard emesis test.

The disclosures of all references mentioned herein (including all patent and scientific documents) are incorporated herein by reference. It will be appreciated that those skilled in the art, upon consideration of this disclosure, may make modifications and improvements within the spirit and scope of this disclosure.

What is claimed is:

1. A method of modulating CB1 receptor binding and activation in an individual or an animal without substantially modulating activity of the receptor, the method comprising administering to the individual or animal a therapeutically effective amount of at least one of the neutral antagonists having the chemical structure of Compound 2 or Compound 3 and physiologically acceptable salts thereof:

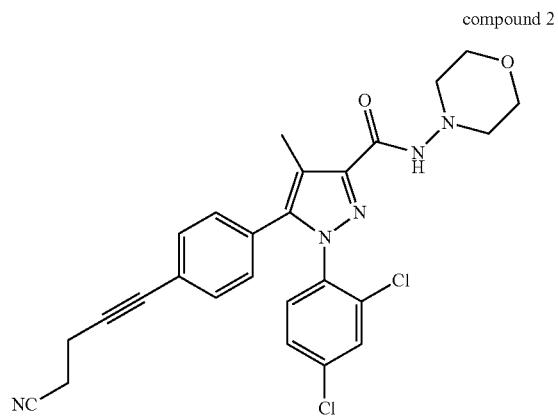

compound 2

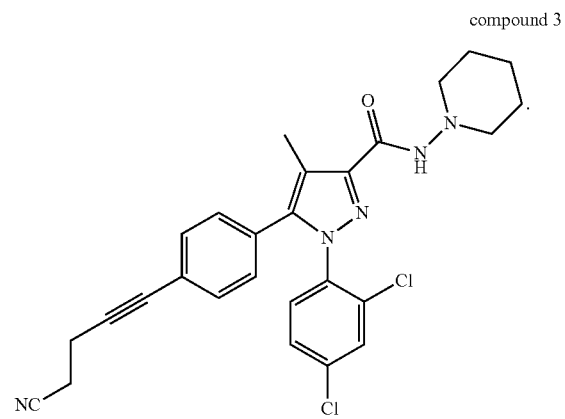

compound 3

2. A method to treat, or reduce a condition chosen from one or more of obesity; appetite disorders; cardiovascular disorders; a metabolic disorder selected from one or more of diabetes, elevated LDL, elevated cholesterol, and low HDL; addiction to drugs of abuse consisting of cannabis, nicotine, cocaine, and/or opiates; loss of cognition and memory; and schizophrenia in an animal or individual having that condition comprising administering to the individual or animal in need of same a therapeutically effective amount of at least one of the compounds having the chemical structure of Compound 2 or Compound 3 and physiologically acceptable salts thereof:

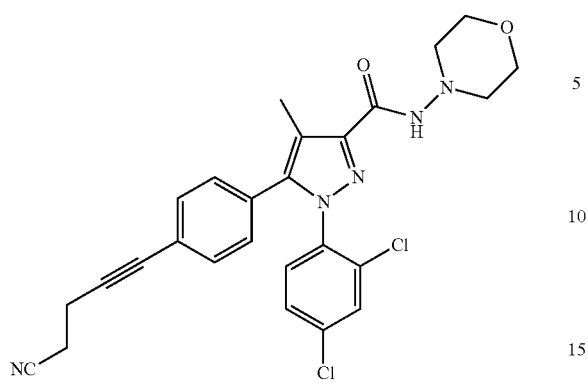

compound 2

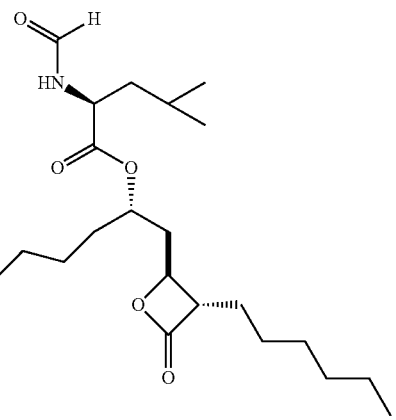

Xenical® (Orlistat) (S)-(S)-1-((2S,3S)-3-hexyl-4-oxooxetan-2-yl)tridecan-2-yl 2-formamido-4-methylpentanoate compound 3

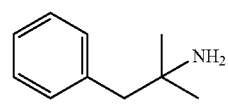

Phentermine
2-methyl-1-phenylpropan-2-amine

3. The method of claim 2, wherein the condition is obesity or an appetite disorder.

4. The method of claim 2, wherein the condition is obesity.

5. A method to treat, or reduce a condition chosen from one or more of obesity; appetite disorders; cardiovascular disorders; a metabolic disorder selected from one or more of diabetes, elevated LDL, elevated cholesterol, and low HDL; addiction to drugs of abuse consisting of cannabis, nicotine, cocaine, and/or opiates; loss of cognition and memory; and schizophrenia, in an animal or individual having that condition comprising administering to the individual or animal in need of same a therapeutically effective amount of at least one of

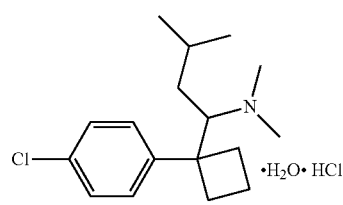

Meridia® (Sibutramine)
1-(1-(4-chlorophenyl)cyclobutyl)-N,N,3-trimethylbutan-1-amine, hydrochloride monohydrate

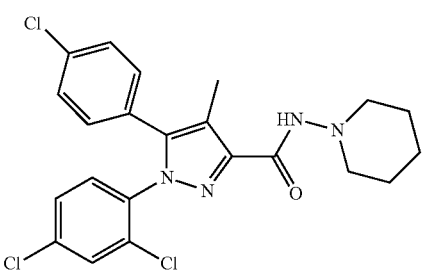

SR141716A (Acomplia®/Rimonabant) 5-(4-chlorophenyl)-1-(2,4-dichlorophenyl)-4-methyl-N-(piperidin-1-yl)-1H-pyrazole-3-carboxamide

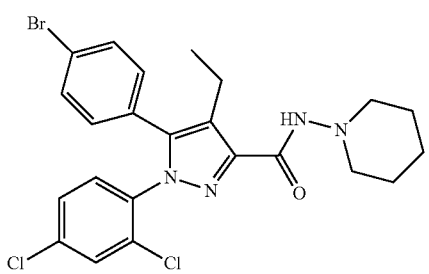

SR147778 (Surinabant) 5-(4-bromophenyl)-1-(2,4-dichlorophenyl)-4-ethyl-N-(piperidin-1-yl)-1H-pyrazole-3-carboxamide -continued

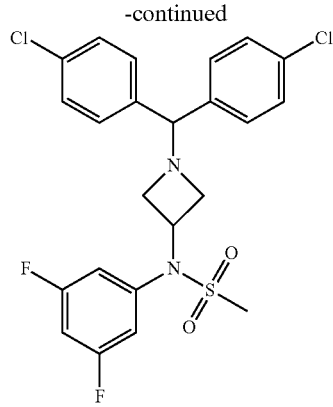

AVE-1625 N-[1-[bis(4-chlorophenyl)methyl]-3-
azetidinyl]-N-(3,5-difluorophenyl)-
methanesulfonamide

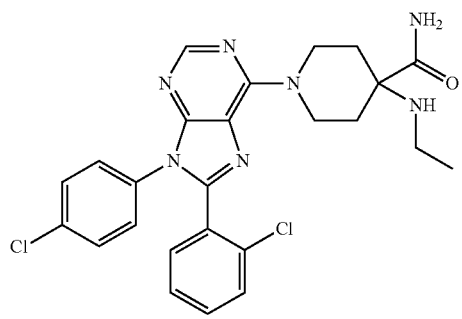

CP-945,598 (Otenabant) 1-[8-(2-Chlorophenyl)-9-(4-
chlorophenyl)-9H-purin-6-yl]-4-(ethylamino)piperidine-
4-carboxamide

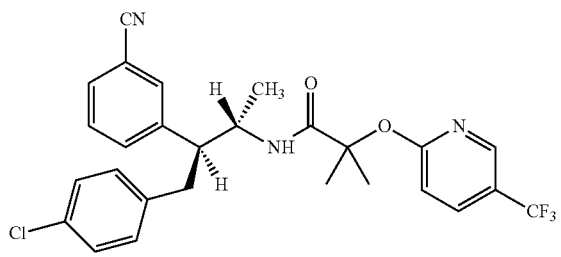

MK-0364 (Taranabant) N-((2S,3S)-4-)4-chlorophenyl)-3-)3-
cyanophentl)butan-2-yl)-2-methyl-2-((5-trifluoromethyl)pyridin-
2-yl)oxy)propanamide

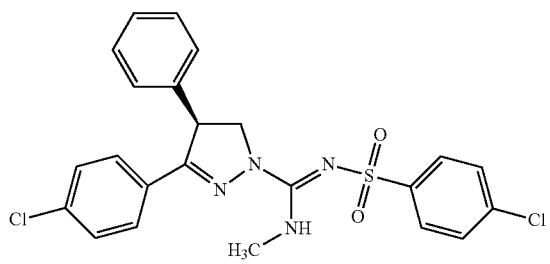

SLV-319 (Ibipinabant) (S,E)-3(4-chlorophenyl)sulfonyl-
N-methyl-4-phenyl-4,5-dihydro-1H-pyrazole-1-
carboximidamide -continued

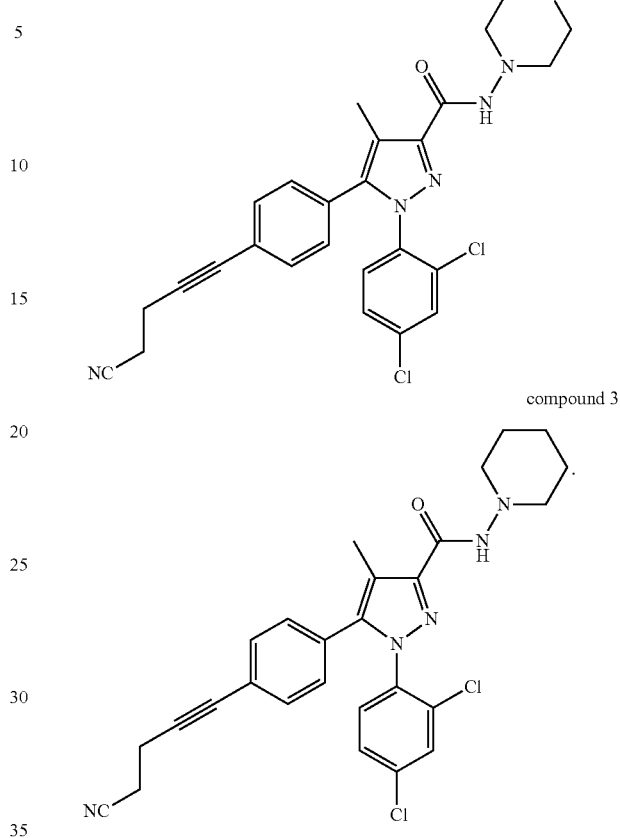

compound 2 compound 3

6. The method of claim 2, wherein the condition is diabetes.

7. The method of claim 2, wherein the condition is a metabolic disorder selected from one or more of diabetes, elevated LDL, elevated cholesterol, and low HDL.

8. The method of claim 2, wherein the condition is elevated cholesterol.

9. The method of claim 2, wherein the condition is cardiovascular disorder.

10. The method of claim 2 wherein the condition is addiction to drugs of abuse consisting of cannabis, nicotine, cocaine, and/or opiates.

11. The method of claim 2 wherein the condition is loss of cognition and/or memory.

12. The method of claim 2 wherein the condition is schizophrenia.

13. The method of claim 2 wherein the condition is low HDL.

14. The method of claim 2 wherein the condition is elevated LDL.

15. The method of claim 2 comprising the individual adopting a lifestyle choice to lose or maintain weight concurrently with administration of at least of the compounds having the chemical structure of Compound 2 or Compound 3 and physiologically acceptable salts thereof.

* * * * *

UNITED STATES PATENT AND TRADEMARK OFFICE
CERTIFICATE OF CORRECTION

PATENT NO. : 8,293,211 B2
APPLICATION NO. : 12/157578
DATED : October 23, 2012
INVENTOR(S) : Makriyannis et al.

It is certified that error appears in the above-identified patent and that said Letters Patent is hereby corrected as shown below:

Column 21, lines 44-46:

delete "MK-0364 (Taranabant) N-((2S,3S)-4-)4-chlorophenyl)-3-)3-cyanophentl) butan-2-yl)-2-methyl-2-((5-trifluoromethyl)pyridin-2-yl)oxy)propanamide"

and insert -- MK-0364 (Taranabant) N-((2S,3S)-4-(4-chlorophenyl)-3-(3-cyanophenyl) butan-2-yl)-2-methyl-2-((5-(trifluoromethyl)pyridin-2-yl)oxy)propanamide --

Column 21, lines 57-59:

delete "SLV-319 (Ibipinabant) (S,E)-3(4-chlorophenyl) sulfonyl-N-methyl-4-phenyl-4,5-dihydro-1H-pyrazole-1-carboximidamide"

and insert -- SLV-319 (Ibipinabant) (S,E)-3-(4-chlorophenyl)-N'-((4-chlorophenyl) sulfonyl)-N-methyl-4-phenyl-4,5-dihydro-1H-pyrazole-1-carboximidamide --

Column 21, line 60:

Insert -- in combination with at least one of the compounds having the chemical structure of Compound 2 or Compound 3 and physiologically acceptable salts thereof: --

Signed and Sealed this
Twenty-second Day of January, 2013

David J. Kappos
*Director of the United States Patent and Trademark Office*